United States Patent
Pitarresi et al.

(10) Patent No.: US 11,285,136 B2
(45) Date of Patent: Mar. 29, 2022

(54) NANOPARTICLES FOR CONTROLLED RELEASE OF SORAFENIB AND SORAFENIB DERIVATIVES

(71) Applicant: DISTRETTO TECNOLOGICO SICILIA MICRO NANO SISTEMI S.C.A.R.L., Catania (IT)

(72) Inventors: Giovanna Pitarresi, Palermo (IT); Melchiorre Cervello, Palermo (IT); Antonina Azzolina, Palermo (IT); Roberto Puleio, Palermo (IT); Guido Ruggero Loria, Palermo (IT); Stefano Puleo, Catania (IT); Gaetano Giammona, Palermo (IT)

(73) Assignee: DISTRETTO TECNOLOGICO SICILIA MICRO E NANO SISTEMI S.C.A.R.L., Catania (IT)

( * ) Notice: Subject to any disclaimer, the term of this patent is extended or adjusted under 35 U.S.C. 154(b) by 207 days.

(21) Appl. No.: 16/486,565

(22) PCT Filed: Feb. 8, 2018

(86) PCT No.: PCT/IB2018/050786
§ 371 (c)(1),
(2) Date: Aug. 16, 2019

(87) PCT Pub. No.: WO2018/150302
PCT Pub. Date: Aug. 23, 2018

(65) Prior Publication Data
US 2020/0000783 A1 Jan. 2, 2020

(30) Foreign Application Priority Data
Feb. 16, 2017 (IT) .................. 102017000017594

(51) Int. Cl.
| | | |
|---|---|---|
| *A61K 31/44* | (2006.01) | |
| *A61K 9/14* | (2006.01) | |
| *A61K 9/19* | (2006.01) | |
| *A61K 47/32* | (2006.01) | |
| *A61K 47/34* | (2017.01) | |

(52) U.S. Cl.
CPC .............. *A61K 31/44* (2013.01); *A61K 9/146* (2013.01); *A61K 9/19* (2013.01); *A61K 47/32* (2013.01); *A61K 47/34* (2013.01)

(58) Field of Classification Search
None
See application file for complete search history.

(56) References Cited

PUBLICATIONS

Yang et al. In vivo biodistribution, biocompatibiity, and efficacy of sorafenib-loaded lipid-based nanosuspensions evaluated experimentally in cancer. International Journal of Nanomedicine, 11, pp. 2329-2343. (Year: 2016).*
Cavallaro et al. New Self-Assembling Polyaspartamide-Based Brush Copolymers Obtained by Atom Transfer Radical Polymerization. Macromolecules, 42, pp. 3247-3257. (Year: 2009).*
Zhang et al. "Preparation, in vitro release, and pharmacokinetics in rabbits of lyophilized injection of solafenib solid lipid nanoparticles" Int J Nanomed 2012, 7:2901-2910.
Kim et al. "Antitumor activity of sorafenib-incorporated nanoparticles of dextran/poly(dl-lactide-coglycolide) block copolymer" Nanoscale Res Lett 2012, 7, 91, 1-6.
Licciardi et al. "PHEA-graft-polybutylmethacrylate copolymer microparticles for delivery of hydrophobic drugs". Int J Pharm 2012, 433:16-24.
Babić et al. "New solafenib derivatives: synthesis, antiproliferative activity against tumour cell lines and antimetabolic evaluation" Molecules 17 (2012) 1124-1137.
Wang et al. "Synthesis and in vitro cytotoxic activities of solafenib derivatives" Chinese Chemical Letters 25 (2014) 702-704.
Craparo et al. "Galactosylated polymeric carriers for liver targeting of Sorafenib." Int J Pharm 2014, 466:172-180.
Cusimano et al., "Cytotoxic activity of the novel small molecule AKT inhibitor SC66 in hepatocellular carcinoma cells." Oncotarget 6, 1707-1722.
International Search Report and Written Opinion for International Patent Application No. PCT/IB2018/050786, dated Feb. 6, 2018, 15 pages.

* cited by examiner

*Primary Examiner* — Jessica Worsham
(74) *Attorney, Agent, or Firm* — Armstrong Teasdale LLP

(57) ABSTRACT

Described herein are loaded nanoparticles of Sorafenib (Sorafenib PBB) or Sorafenib derivatives (Sorafenib PBB derivatives), wherein the nanoparticles are polymeric PBB nanoparticles, (PHEA-BIB-pButMA, α,β-poly(N-2-hydroxyethyl)-co-{N-2-ethylene-[2-(poly(butylmethacrylate)-isobutyrate]}-D, L-aspartamide, as well as a method for obtaining them.
Also described herein are a controlled release formulation of Sorafenib or Sorafenib, derivatives that include Sorafenib PBB or Sorafenib PBB derivatives, and to the use of the formulation in the treatment of tumor diseases of the kidney, liver, thyroid, colon, breast, pancreas, lungs and/or recurrent glioblastoma.

20 Claims, 6 Drawing Sheets

NANOPARTICLES FOR CONTROLLED RELEASE OF SORAFENIB AND SORAFENIB DERIVATIVES

CROSS-REFERENCE TO RELATED APPLICATIONS

This application is a U.S. National Phase Application of International Patent Application No. PCT/IB2018/050786, filed Feb. 8, 2018, which claims the benefit of priority to Italian Patent Application No. 102017000017594, filed Feb. 16, 2017, the entire contents of which are hereby incorporated by reference herein.

FIELD OF THE INVENTION

The present invention relates to loaded nanoparticles of Sorafenib (Sorafenib PBB) or Sorafenib derivatives (Sorafenib PBB derivatives), where said nanoparticles are polymeric PBB nanoparticles, (PHEA-BIB-pButMA, α,β-poly(N-2-hydroxyethyl)-co-{N-2-ethylene-[2-(poly(butyl-methacrylate)-isobutyrate]}-D,L-aspartamide, and to a method for obtaining them.

The present invention further relates to a controlled release formulation of Sorafenib or Sorafenib derivatives, which comprises Sorafenib PBB or Sorafenib PBB derivatives, and to the use of said formulation in the treatment of tumor diseases of the kidney, liver, thyroid, colon, breast, pancreas, lungs and/or recurrent glioblastoma.

BACKGROUND ART

Sorafenib, 4-[4-[[4-chloro-3-(trifluoromethyl)phenyl]carbamoylamino]phenoxy]-N-methyl-pyridine-2-carboxamide, is an approved drug for the treatment of hepatocellular carcinoma (HCC). The mechanism of action is mediated by the inhibitory activity exerted on kinases overexpressed in a series of molecular pathways involved in the transformation of normal cells into tumor cells, in particular receptors with kinase activity and on Raf kinases.

The drug is commercially available as orally administered tablets. Sorafenib is poorly soluble in water and its bioavailability is low due to a strong first-pass effect. In addition, often significant gastrointestinal irritation is associated with administration (Zhang et al. *Preparation, in vitro release, and pharmacokinetics in rabbits of lyophilized injection of Sorafenib solid lipid nanoparticles*. Int J Nanomed 2012, 7:2901-2910). Other side effects such as skin rash, diarrhea, hypertension strongly limit the clinical application thereof.

Kim D H et al. in Antitumor activity of Sorafenib-incorporated nanoparticles of dextran/poly(dl-lactide-coglycolide) block copolymer. Nanoscale Res Lett 2012, 7, 91, 1-6 described nanoparticles for the controlled release of Sorafenib. Sorafenib was incorporated into a dextran/poly (dl-lactide-co-glycolide) copolymer (DexbLG), with a copolymer/Sorafenib ratio between 40:2 and 40:7, resulting in rather homogeneous spherical nanoparticles. The formulation proved to be cytotoxic on cholangiocarcinoma cells with similar activity to that of free Sorafenib. The work provides no indication of a preferential distribution in tumor tissue for said nanoparticles.

Aiming at providing an advantageous alternative to the currently available formulations in the prior art, polymeric nanoparticles comprising Sorafenib, or Sorafenib derivatives, are described herein, which have shown surprisingly advantageous features in terms of release efficacy and stability over time.

BRIEF DESCRIPTION OF THE INVENTION

The present invention relates to polymeric nanoparticles containing Sorafenib or Sorafenib derivatives. The present invention further relates to a method for preparing said particles and to their use in the treatment of tumor diseases of the kidney, liver, thyroid, colon, breast, pancreas, lungs and/or recurrent glioblastoma.

The nanoparticles were obtained from a biocompatible polymer, α,β-poly(N-2-hydroxyethyl)-D,L-aspartamide (PHEA) (Giammona et al. *Reaction of α,β-poly(N-hydroxyethyl)-dl-aspartamide with derivatives of carboxylic acids*. J Polymer Sci Polymer Chem. 1987, 25:2813-2818; Mendichi et al. *Molecular characterization of α,β- poly(N-2-hydroxyethyl)-dl-aspartamide derivatives as potential self-assembling copolymers forming polymeric micelles*. Polymer 2003, 44:4871-4879). In summary, PHEA was derivatized with α-bromoisobutyryl bromide (BIB), and the derivative thus obtained was used as a "macroinitiator" for the polymerization of butyl methacrylate (ButMA), lateral chain polymerization and via Atom Transfer Radical Polymerization (ATRP) (Cavallaro et al. *New Self-Assembling Polyaspartamide-Based Brush Copolymers Obtained by Atom Transfer Radical Polymerization*. Macromolecules 2009, 42:3247-3257; Licciardi et al. *PHEA-graft-polybutylmethacrylate copolymer microparticles for delivery of hydrophobic drugs*. Int J Pharm 2012, 433:16-24; Licciardi et al. *Polymeric nanocarriers for magnetic targeted drug delivery: preparation, characterization and in vitro and in vivo evaluation*. Mol Pharm 2013, 10:4397-4407). The nanoparticles thus obtained were loaded with the drug by means of the dialysis method, without the use of surfactants, and characterized.

DETAILED DESCRIPTION OF THE INVENTION

Figure 1:
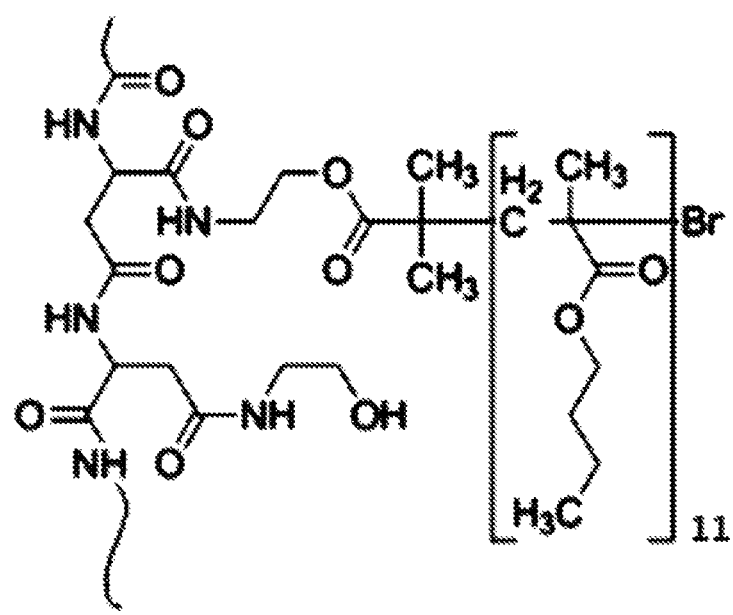
FIG. 1: Chemical structure of PHEA-BIB-pButMA copolymer (PBB).

For loading the nanoparticles with the drug, the PBB copolymer, synthesized by ATRP as described in the aforementioned Cavallaro et al. 2009, Licciardi et al. 2012, Licciardi et al. 2013, and whose chemical structure is shown in FIG. 1, was dissolved in a solvent, for example selected from the group comprising dimethylformamide (DMF), dimethyl sulfoxide (DMSO), tetrahydrofuran (THF) or mixtures thereof, in the presence of Sorafenib or a derivative of Sorafenib, with a weight ratio of copolymer to Sorafenib or Sorafenib derivative between 10:1 and 1:1, preferably between 6:1 and 1.5:1, even more preferably 2:1, and the solution was dialyzed for three hours against bidistilled water using a dialysis membrane with a molecular weight (MW) cut-off higher than the polymer MW, i.e. higher than 80,000 Da, preferably higher than or equal to 100,000 Da.

In a preferred embodiment, said nanoparticles are loaded with Sorafenib (Sorafenib PBB), or with Sorafenib derivatives or pharmaceutically acceptable salts thereof (Sorafenib PBB derivatives). For the purposes of the present invention, the term "Sorafenib derivatives" means, by way of example, the following compounds: Regorafenib, of formula (1)

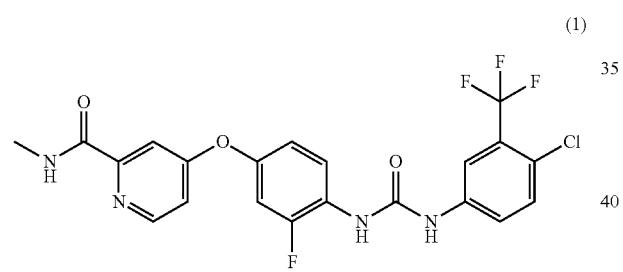

(1)

Dimeric derivatives, such as for example SC-60 of formula (2)

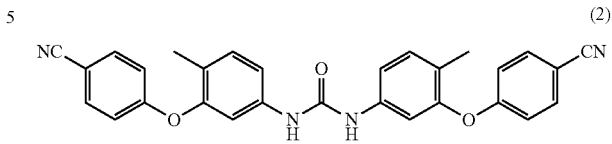

(2)

HLC-80, of formula (3)

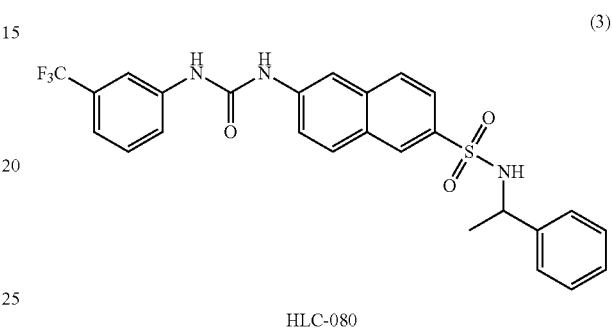

(3)

HLC-080

Other Sorafenib derivatives are described in Chen Kuen-Feng et al., *Blockade of STATS activation by sorafenib derivatives through enhancing SHP-1 phosphatase activity*, Eur J Med Chem 55 (2012) 220-227, of general formula (4), where R1, R2 and R3 are as indicated in table 1 below.

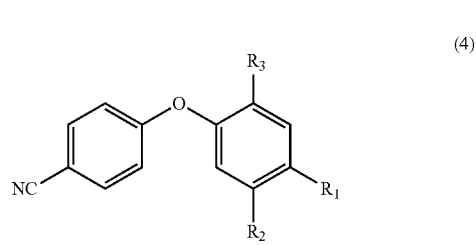

(4)

TABLE 1

| Cpd | R$_1$ | R$_2$ | R$_3$ |
|---|---|---|---|
| SC-1 | ![structure with Cl and CF3] | | |
| 1 | ![structure with dimethoxybenzyl] | H | H |

TABLE 1-continued

| Cpd | R₁ | R₂ | R₃ |
|---|---|---|---|
| 2 | [structure: -CH₂-NH-C(=O)-NH-(4-chloro-3-trifluoromethylphenyl)] | H | H |
| 3 | [structure: -CH₂-NH-C(=O)-NH-CH₂-(3,4-dimethoxyphenyl)] | H | H |
| 4 | [structure: -CH₂-NH-C(=O)-NH-CH₂-(3-trifluoromethoxyphenyl)] | H | H |
| 5 | [structure: -NH-C(=O)-NH-CH(CH₃)-(1-naphthyl)] | H | H |
| 6 | H | [structure: -NH-C(=O)-NH-(4-chloro-3-trifluoromethylphenyl)] | H |
| 7 | H | [structure: -NH-S(=O)₂-(3-trifluoromethylphenyl)] | H |
| 8 | H | [structure: -NH-CH₂-(3-trifluoromethoxyphenyl)] | H |
| 9 | H | H | [structure: -NH-C(=O)-NH-(3-fluorophenyl)] |

TABLE 1-continued

| Cpd | R₁ | R₂ | R₃ |
|---|---|---|---|
| 10 | H | (benzamide group) | H |
| 11 | H | (benzenesulfonamide group) | H |
| 12 | H | (urea linked to 4-chloro-3-trifluoromethylphenyl) | Me |

Described in the same work are the derivatives of general formula (5), where R1 and R2 are as described in table 2.

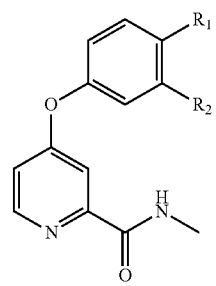

(5)

TABLE 2

| Cpd | R₁ | R₂ |
|---|---|---|
| 13 | H | (urea linked to 3-fluorophenyl) |
| 14 | H | (sulfonamide with 3-CF₃ phenyl) |
| 15 | H | (benzamide group) |

TABLE 2-continued

| Cpd | R₁ | R₂ |
|---|---|---|
| 16 | H | (NH-CH₂-3-OCF₃-phenyl) |
| 17 | H | (benzenesulfonamide) |

Again described in Chen et al. are the derivatives of general formula (6) where R1, R2 and R3 are as described in table 3.

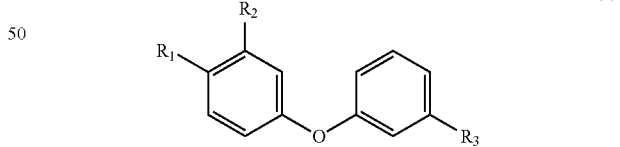

(6)

TABLE 3

| Cpd | R₁ | R₂ | R₃ |
|---|---|---|---|
| 18 | NO₂ | NH₂ | 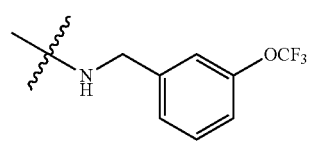 [SMILES: *NCc1cccc(OC(F)(F)F)c1] |

TABLE 3-continued

| Cpd | R₁ | R₂ | R₃ |
|---|---|---|---|
| 19 | NO₂ | NH₂ | (N-sulfonyl-3-trifluoromethylphenyl) |
| 20 | NO₂ | NH₂ | (urea linked to 4-chloro-3-trifluoromethylphenyl) |
| 21 | NH₂ | NH₂ | (NH-CH₂-3-trifluoromethoxyphenyl) |
| 22 | NH₂ | NH₂ | (N-sulfonyl-3-trifluoromethylphenyl) |
| 23 | (urea) | | (NH-CH₂-3-trifluoromethoxyphenyl) |
| 24 | (urea) | | (N-sulfonyl-3-trifluoromethylphenyl) |

Further Sorafenib derivatives are those described in Zhang L et al., *Synthesis and anti-proliferative activity evaluation of sorafenib derivatives with a 3-arylacryloyl hydrazide unit*, Med Chem Res 24 (2015) 1733-1743, of general formula (7):

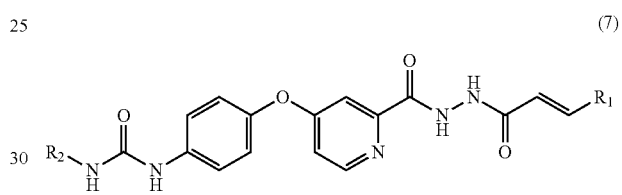

(7)

where R1 and R2 are as described in table 4 below.

TABLE 4

| Compound | R₂ | R₁ |
|---|---|---|
| Sorafenib | — | — |
| 8a | 4-Chloro-3-trifluoromethylphenyl | Phenyl |
| 8b | 4-Chloro-3-trifluoromethylphenyl | 2-Furyl |
| 8c | 4-Chloro-3-trifluoromethylphenyl | 3-Furyl |
| 8d | 4-Chloro-3-trifluoromethylphenyl | 2-Thienyl |
| 8e | 4-Chloro-3-trifluoromethylphenyl | Pyridine-3-yl |
| 8f | 4-Chloro-3-trifluoromethylphenyl | 4-Hydroxyphenyl |
| 8 g | 4-Chloro-3-trifluoromethylphenyl | 4-Methoxyphenyl |
| 8 h | 4-Chloro-3-trifluoromethylphenyl | 4-Chlorophenyl |
| 8i | 4-Chloro-3-trifluoromethylphenyl | 4-Trifluoromethylphenyl |
| 8j | 4-Chloro-3-trifluoromethylphenyl | 4-Carbomethoxyphenyl |
| 8k | 4-Chloro-3-trifluoromethylphenyl | 3-Hydroxyphenyl |
| 8l | 4-Chloro-3-trifluoromethylphenyl | 3-Chlorophenyl |
| 8m | 4-Chloro-3-trifluoromethylphenyl | 3-Trifluoromethylphenyl |
| 8n | 4-Chloro-3-trifluoromethylphenyl | 4-Hydroxyl-3-methoxylphenyl |
| 8o | 4-Chloro-3-trifluoromethylphenyl | 3,4-Bimethoxylphenyl |
| 8p | 4-Chloro-3-trifluoromethylphenyl | 4-Acetoxy-3-methoxylphenyl |
| 8q | 4-Chloro-3-trifluoromethylphenyl | 3,4-Bifluorophenyl |
| 8r | 4-Chloro-3-trifluoromethylphenyl | 2,4-Bichlorophenyl |
| 8 s | 4-Chloro-3-trifluoromethylphenyl | 2,3,4,5,6-Pentafluorophenyl |
| 11a | 4-Chlorophenyl | 4-Chlorophenyl |
| 11b | 4-Flurophenyl | 4-Chlorophenyl |
| 11c | 4-Trifluoromethylphenyl | 4-Chlorophenyl |
| 11d | 4-Ethoxylphenyl | 4-Chlorophenyl |
| 11e | 3-Methylphenyl | 4-Chlorophenyl |
| 11f | 3-Bromophenyl | 4-Chlorophenyl |
| 11g | 3-Chloro-4-methylphenyl | 4-Chlorophenyl |
| 11h | 2,4-Biflourophenyl | 4-Chlorophenyl |

Further derivatives of Sorafenib are described in Wu C et al. *Design, synthesis and biological evaluation of phenylpicolinamide sorafenib derivatives as antitumor agents* Med Chem Res (2017) DOI 10.1007/s00044-017-2045-0. Among these are compounds 12 and 13 of formula (8) and compounds 14a-k e 15a-k of formula (9) and (10), respectively, where R is as described in table 5.

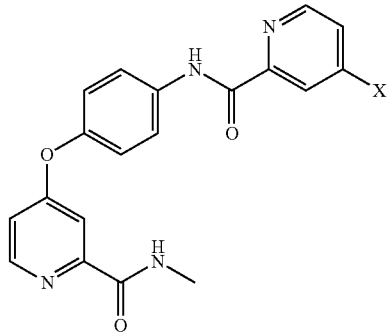

(8)

12, X = Cl
13, X = Br

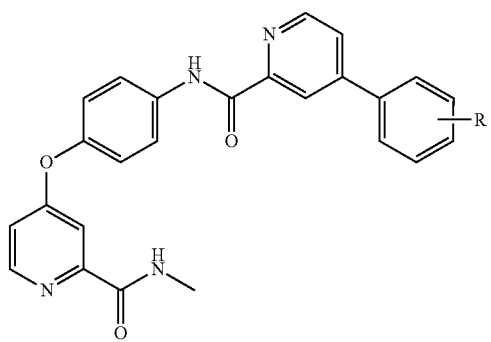

(9)

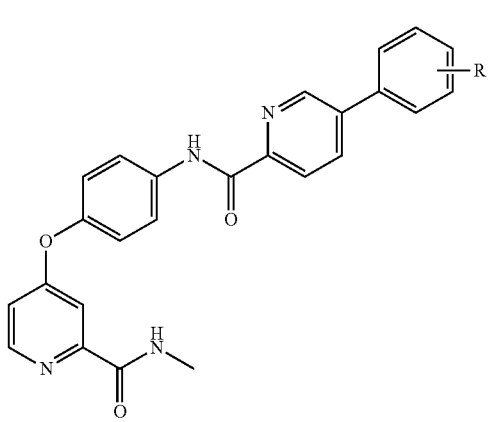

(10)

15a-k

TABLE 5

| Comp. no. | R |
|---|---|
| 12 | — |
| 13 | — |
| 14a | H |
| 14b | 4-F |
| 14c | 2,4-di F |

TABLE 5-continued

| Comp. no. | R |
|---|---|
| 14d | 4-Cl |
| 14e | 4-OCH$_3$ |
| 14f | 4-CH$_3$ |
| 14g | 3-CH$_3$ |
| 14h | 3-F |
| 14i | 4-CF$_3$ |
| 14j | 4-CH$_2$CH$_3$ |
| 14k | 2,4-di CH$_3$ |
| 15a | H |
| 15b | 4-F |
| 15c | 2,4-di F |
| 15d | 4-Cl |
| 15e | 4-OCH$_3$ |
| 15f | 4-CH$_3$ |
| 15g | 3-CH$_3$ |
| 15h | 3-F |
| 15i | 4-CF$_3$ |
| 15j | 4-CH$_2$CH$_3$ |
| 15k | 2,4-di CH$_3$ |

Further derivatives of Sorafenib are described in Babic Z et al. *New sorafenib derivatives: synthesis, antiproliferative activity against tumour cell lines and antimetabolic evaluation* Molecules (2012) 1124-1137. Among these are compounds 2a-e, 3a-e, 4a-e of formula (11), (12) and (13), respectively, where R is as described in table 6.

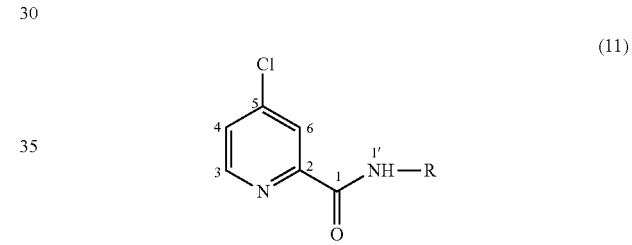

(11)

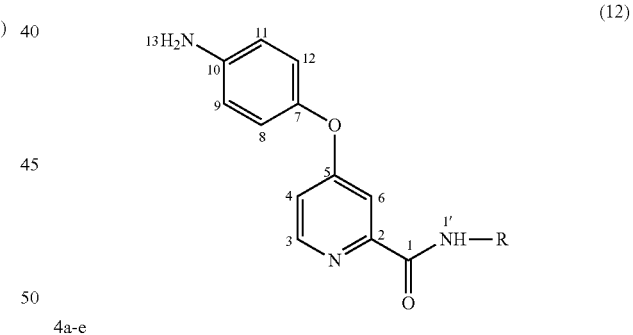

(12)

4a-e

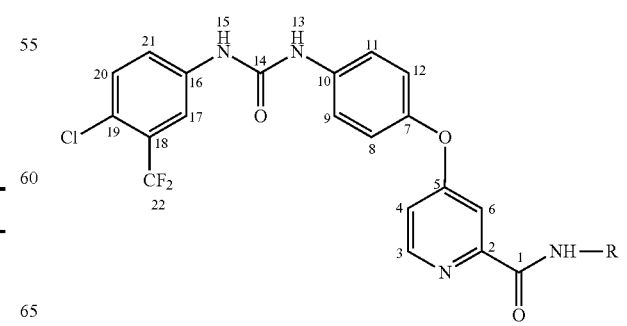

(13)

TABLE 6
| Compd. | R |
|---|---|
| 2a | 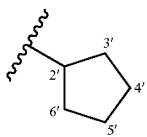 |
| 2b | 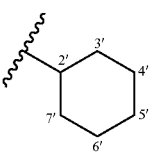 |
| 2c | 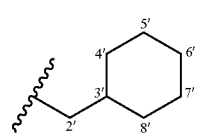 |
| 2d | 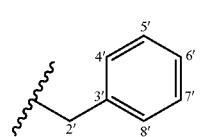 |
| 2e | 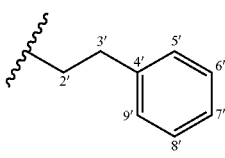 |
| 3a | 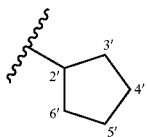 |
| 3b | 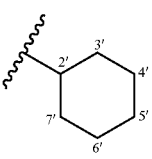 |
| 3c | 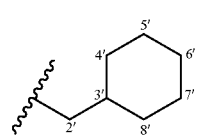 |
| 3d | 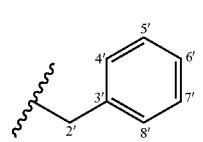 |
| 3e | 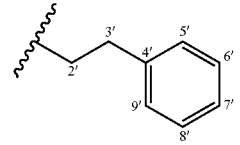 |
| 4a | 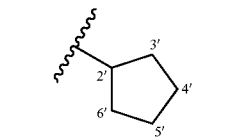 |
| 4b | 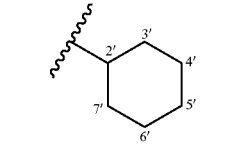 |
| 4c | 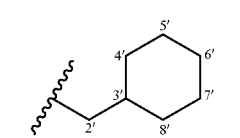 |
| 4d | 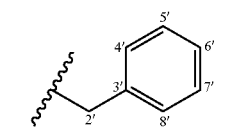 |
| 4e | 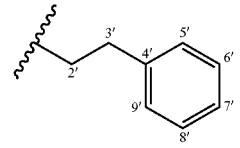 |
Further derivatives are derivatives of general formula (14), described in Wang K et al. *Synthesis and in vitro cytotoxic activities of sorafenib derivatives* Chinese Chemical Letters 25 (2014) 702-704, where R is as shown in table 7.
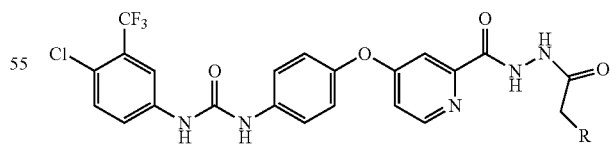
(14)
TABLE 7
| Compd. | Substituent (R) |
|---|---|
| 5a | $C_6H_4$ |
| 5b | $4\text{-}ClC_6H_4$ |
| 5c | $3\text{-}ClC_6H_4$ |

TABLE 7-continued

| Compd. | Substituent (R) |
|---|---|
| 5d | 2-ClC$_6$H$_4$ |
| 5e | 3-CF$_3$C$_6$H$_4$ |
| 5f | 4-CF$_3$C$_6$H$_4$ |
| 5g | 3-FC$_6$H$_4$ |
| 5h | 4-FC$_6$H$_4$ |
| 5i | 3-F-5-FC$_6$H$_3$ |
| 5j | 3-F-4-BrC$_6$H$_3$ |
| 5k | 2-F-3-FC$_6$H$_3$ |
| 5l | 3-Cl-4-OHC$_6$H$_3$ |
| 5m | 2-OMeC$_6$H$_4$ |
| 5n | 3-OMe-4-OMeC$_6$H$_3$ |
| 5o | 4-OEtC$_6$H$_4$ |
| 5p | 2-Naphthyl |
| 5q | 4-C$_6$H$_5$—C$_6$H$_4$ |
| 5r | 4-MeC$_6$H$_4$ |

Those skilled in the art know how to modify the structure of Sorafenib so as to obtain further derivatives, which derivatives are to be understood as included in the definition of "Sorafenib derivatives" according to the present invention.

In one embodiment, said Sorafenib or Sorafenib derivatives are in the form of pharmaceutically acceptable salts.

In a preferred embodiment, said Sorafenib is Sorafenib tosylate.

In the process of preparing the nanoparticles according to the present invention, the external aqueous phase is gently stirred with a magnetic stirrer, so as to favor the diffusion process. Bidistilled water is periodically replaced, typically at intervals of 5 hours, or 4 hours, or 3 hours. Dialysis is performed over a period of approximately 24 hours. At the end, a cryoprotectant is optionally added, preferably selected from the group comprising PVP (polyvinylpyrrolidone) and/or PVA (polyvinyl alcohol) and/or trehalose and/or lactose and/or mixtures thereof, preferably in a copolymer/cryoprotective weight ratio=1:1, and the resulting dispersion is filtered through a 5 μm membrane filter, so as to remove the insoluble material. The filtrate is lyophilized, so as to have lyophilized PBB nanoparticles loaded with Sorafenib (Sorafenib PBB) or Sorafenib derivatives (Sorafenib PBB derivatives).

The amount of Sorafenib or Sorafenib derivatives loaded into the PBB nanoparticles, i.e. the drug-mass portion of the nanoparticles (drug loading), is determined by high performance liquid chromatography (HPLC). The drug loading percentage (DL %) of Sorafenib PBB was calculated according to Equation (1):

$$DL(\% \ w/w) = \frac{\text{amount of } Sorafenib \text{ in nanoparticles}}{\text{amount of nanoparticles} + Sorafenib} \times 100 \quad (1)$$

The data obtained show a DL % between 0.5 and 30%, preferably between 3 and 20%, even more preferably between 3 and 4%. The efficacy of Sorafenib PBB on the growth of tumor cells was evaluated in an in vitro assay conducted on human hepatocellular carcinoma cells. The results, shown in FIG. 3, show that the entrapment of Sorafenib in PBB not only does not cause a reduction in the activity of the drug but actually increases it, as shown in table 8, which shows the average IC50 values for free Sorafenib and Sorafenib PBBs obtained in HepG2 and Hep3B hepatocellular carcinoma cells.

Figure 3:
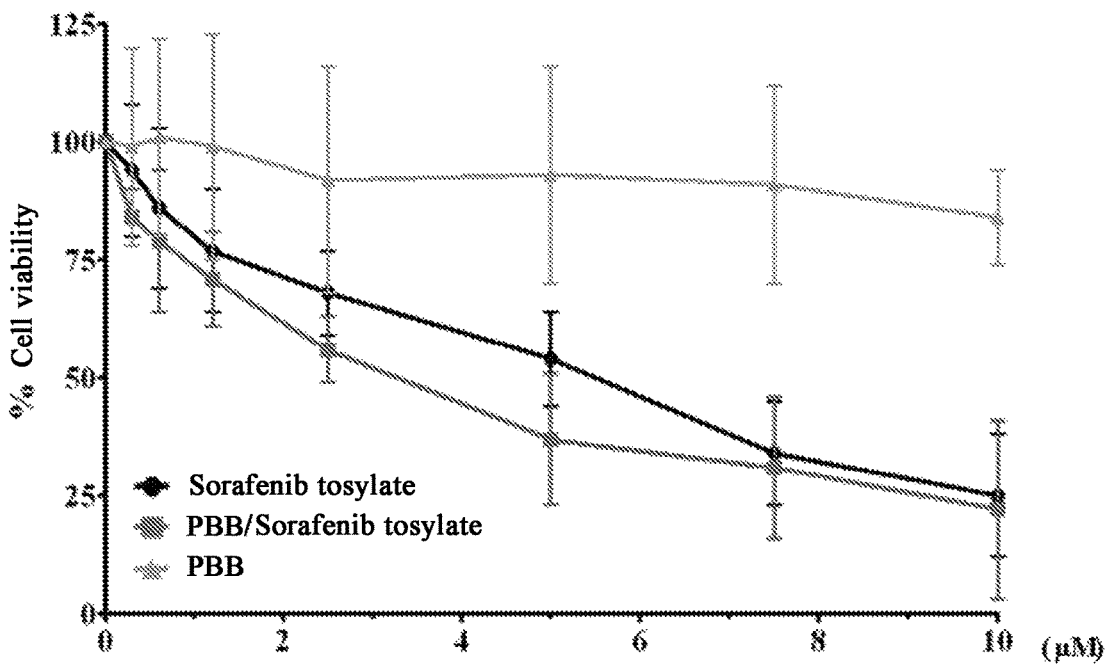
FIG. 3: Effects of Sorafenib in free form, PBB and PBB/Sor on the cell viability of HepG2 (A) and Hep3B (B) hepatic carcinoma cells. Cell viability is expressed as a percentage of measured absorbance compared to control cells. The values are expressed as mean±SD of the values obtained in three independent experiments, each performed in triplicate.
Figure 3:
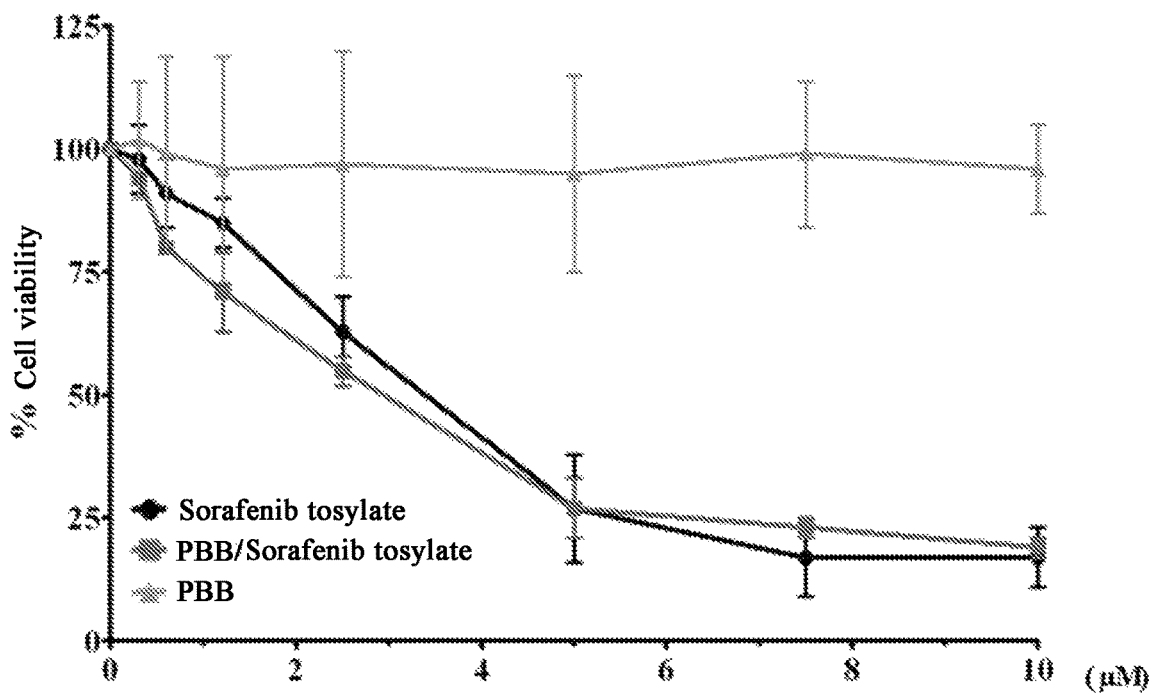

The empty nanoparticles have no cytotoxic effect on the cells tested, as shown in FIG. 3.

TABLE 8

| | Sorafenib (μM) ± DS | Sorafenib PBB (μM) ± DS |
|---|---|---|
| HepG2 | 5.5 ± 1.0 | 3.6 ± 1.1 |
| Hep3B | 3.5 ± 0.5 | 3.0 ± 0.3 |

Figure 4:
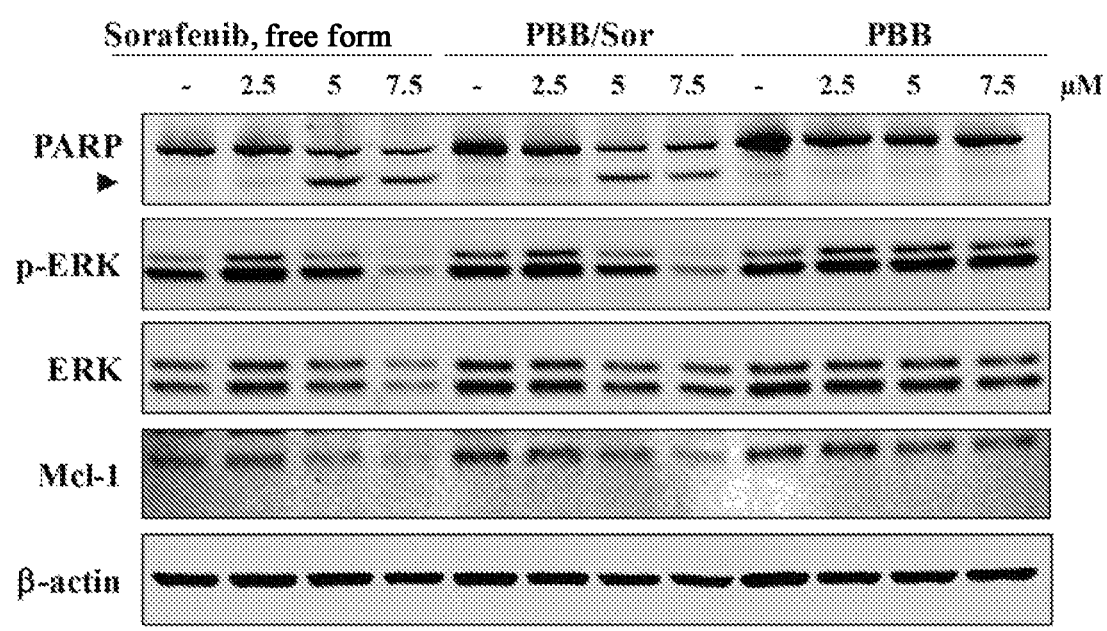
FIG. 4: Effect of Sorafenib in free form, PBB and PBB/Sor on proteins involved in apoptosis and on signaling proteins. The data shown are representative of two independent experiments with comparable results. The arrow indicates the fragment of the PARP protein, produced after activation of the apoptotic response.

The activity of Sorafenib PBB is confirmed by Western blot data reported in FIG. 4 which confirm the low cytotoxic effect of the carrier as well as the maintenance at the molecular level of the free Sorafenib activity by Sorafenib PBB.

Tests conducted in vivo on nude mice in which hepatocellular carcinoma cells were injected showed that Sorafenib PBB enhances the activity of Sorafenib in inhibiting the growth of cancer cells, as well as promoting an overall improvement in the state of the animal.

Figure 6:
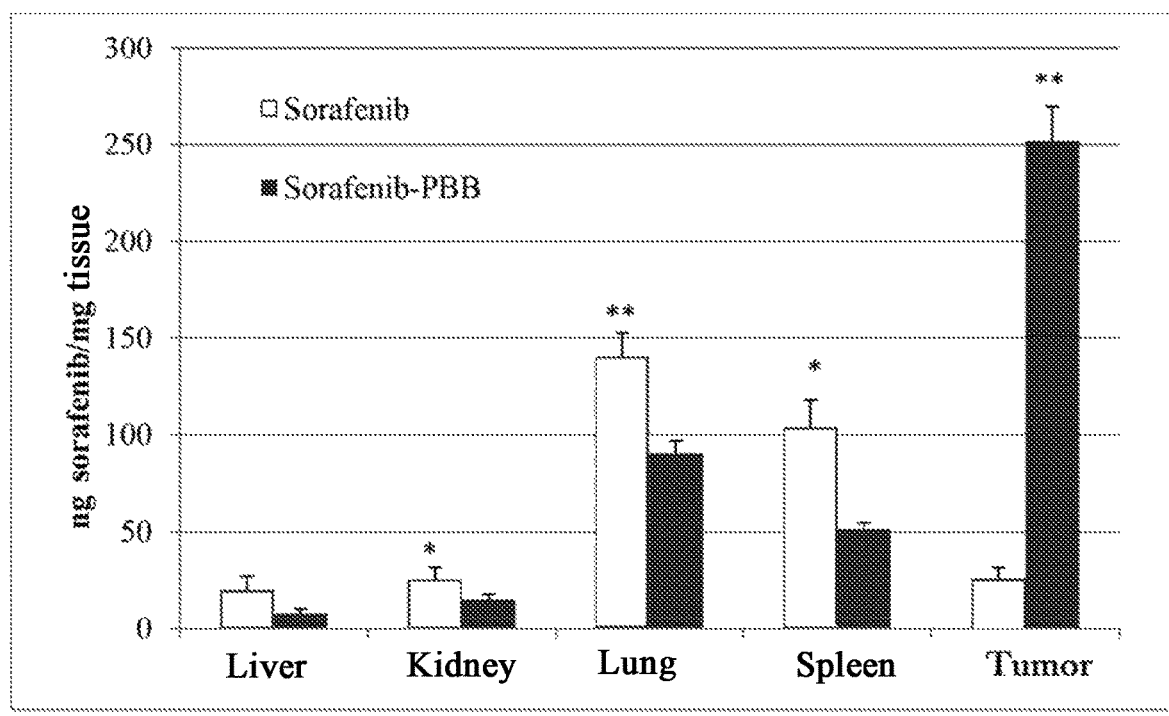
FIG. 6: ng of drug found in the indicated tissues after exposure to free Sorafenib (white columns) or Sorafenib PBB (gray columns) *p<0.05; **p<0.01.

The surprisingly advantageous efficacy observed in vivo is possible due to the preferential accumulation of Sorafenib PBB in the tumor site, as shown in FIG. 6.

The present invention further relates to a formulation for the controlled release of Sorafenib or Sorafenib derivatives, where said formulation comprises Sorafenib PBB or Sorafenib PBB derivatives.

Sorafenib PBB or Sorafenib PBB derivatives are surprisingly advantageous for the treatment of tumor diseases of the kidney, liver, thyroid, colon, breast, pancreas, lungs and/or recurrent glioblastoma, preferably in the treatment of hepatocellular carcinoma. PBP Sorafenib or Sorafenib PBB derivatives proved to release the drug preferentially in the tumor site, resulting in a marked increase in drug efficacy and a reduction of the side effects due to the specific and general distribution of the drug in other organs.

A method for treating a solid tumor in an individual is also described, comprising administering to said individual an effective amount of a composition comprising Sorafenib PBB or Sorafenib PBB derivatives, where said method reduces the viability of hepatocellular carcinoma cells.

In a further embodiment, said method also comprises administering an effective amount of one or more further therapeutic agents.

A further advantage of the Sorafenib PBB or Sorafenib PBB derivatives according to the present invention is to be found in the stability of Sorafenib PBB and Sorafenib PBB derivatives. The physical interactions in the PBB nanoparticles when loaded with Sorafenib or Sorafenib derivatives are sufficiently strong to impart stability during storage at different temperatures, as shown in example 2 below.

EXAMPLES

Example 1: Preparation of Either Empty or Sorafenib-Containing PBB Nanoparticles The PBB copolymer (10 mg) alone or with Sorafenib tosylate (6.35 mg) (weight ratio of copolymer to Sorafenib equal to 2:1) was dissolved in 5 ml of DMF and the solution was dialyzed against 1000 ml of bidistilled water for 3 hours using a SpectraPor dialysis membrane with a 100,000 Da molecular weight cut-off at room temperature. The external aqueous phase was gently stirred with a magnetic stirrer to aid the diffusion process. Then, bidistilled water was replaced at 3-hour intervals for 24 hours. After dialysis, PVP was added to the colloidal dispersion as a cryoprotectant (weight ratio of copolymer to PVP equal to 1:1); the resulting dispersion was filtered through a 5 μm membrane filter (Sartorius, Minisart syringe filter, Germany) to remove the insoluble material and the filtrate was lyophilized.

Example 2: Characterization of the PBB Nanoparticles

The mean size, the polydispersion index (PDI) and the zeta potential of PBB nanoparticles, either empty or loaded with Sorafenib, were evaluated by Dynamic Light Scattering (DLS) measurements using the Malvern Zetasizer NanoZS instrument. Dispersions of nanoparticles were prepared by the method described in example 1 and were analyzed at 25° C. with a sample concentration of 0.5 mg/ml in bidistilled water. The PDI and average hydrodynamic diameter values (size in nm) were obtained by cumulative analysis of the correlation function. The value of the Zeta potential (mV) was calculated by measures of electrophoretic mobility using the Smoluchowsky relation and assuming that k is greater than or equal to 1 (where "k" and "a" are the Debye-Huckel parameter and the radius of the particle, respectively). All measurements were made in triplicate.

The results are shown in Table 9:

TABLE 9

| Nanoparticles | Average diameter (Z average, nm) | PDI | Zeta potential (mV) |
|---|---|---|---|
| PBB | 196 ± 7.6 | 0.32 ± 0.06 | −21.9 ± 4.5 |
| Sorafenib-containing PBB | 240 ± 7.7 | 0.30 ± 0.07 | −28.9 ± 5.7 |

Empty PBB nanoparticles showed an average diameter of about 196 nm; PBB nanoparticles loaded with Sorafenib have an average diameter of less than 500 nm, or 300 nm, preferably between 200 and 280 nm, even more preferably about 240 nm.

The incorporation of the drug increases the average size of the nanoparticles, presumably due to an increase in size in the hydrophobic nucleus due to the presence of the drug itself. The values of the Zeta potential for either empty or Sorafenib-containing nanoparticles are negative, thus confirming the stability of the PBB nanoparticles. Since the value of the Zeta potential does not change significantly after the incorporation of the drug, this result indicates the absence of ionic interactions between Sorafenib and the PBB nanoparticles. The physical stability of the Sorafenib-containing PBB nanoparticles (Sorafenib PBB) was then tested. Aqueous dispersions of Sorafenib PBB were lyophilized and stored at −20, 4 and 25° C. for three months. In the three cases, the ratio of the particle size after storage to the initial size was not greater than 1.0±0.1, thus indicating stability in all the conditions analyzed. Furthermore, Sorafenib PBB was found to maintain the Sorafenib content unchanged under the conditions analyzed.

Example 3: Determination of the Amount of Sorafenib Loaded

The amount of Sorafenib loaded into the PBB nanoparticles, or drug loading, was determined by high performance liquid chromatography (HPLC), using an Agilent 1260 Infinity system with a multiple wavelength detector, MWD, operating at 264 nm. The chromatographic procedure was conducted in isocratic at 25° C., using an inverse phase column Gemini C6-phenyl 110A (Phenomenex 5 μm, 250× 4.60 mm), 90:10 methanol-water as a mobile phase, with a flow of 1 ml/min. 50 μl of sample were injected into the column (Craparo et al. *Galactosylated polymeric carriers for liver targeting of Sorafenib*. Int J Pharm 2014, 466:172-180). Data analysis was performed using Open Lab Chemstation software. The lyophilized nanoparticles containing Sorafenib were suspended in an appropriate amount of methanol and vigorously stirred for 3-4 hours to extract the drug. The resulting solution was centrifuged at 6000 rpm for 10 min at 25° C. and the supernatant was used to determine the drug concentration by a calibration curve obtained with standard Sorafenib solution in methanol in the range 0.4-200 μg/ml ($t_r$=4.3 min). The DL % was found to be 3.8±0.48% w/w.

Example 4: Release of Sorafenib from Sorafenib PBB In Vitro

Release studies of Sorafenib from Sorafenib PBB were performed in vitro in the following receiving media: hydrochloric acid solution (pH 1) to simulate gastric fluid (SGF); phosphate buffer (pH 6.8), to simulate intestinal fluid (SIF) and phosphate buffer solution (PBS) (pH 7.4), i.e. in physiological fluid, using the dialysis tube method with a cut-off of 12000-14000 Da under sink conditions.

An adequate amount of lyophilized Sorafenib PBB was dispersed in 2 ml of the receiving medium at room temperature. The dispersion was then introduced into a dialysis tube which was immersed in an external vessel containing 10 ml of the same medium in the presence of Tween 80 (1% v/v), added as a solubilizer of Sorafenib, slightly soluble in water. During the experiment, the temperature was maintained at 37° C. in a thermostatic stirrer and with stirring of 100 rpm. At scheduled time intervals, 1 ml aliquots were taken from the external medium and replaced with an equal volume of fresh receiving medium. The released Sorafenib was quantified by HPLC analysis. Each in vitro release experiment was repeated in triplicate.

A control experiment was also carried out to determine the dissolution of the free drug: an appropriate amount of Sorafenib was dispersed in the receiving medium, in order to have a final concentration of Sorafenib equal to that present in the nanoparticles, the dispersion was then introduced into a dialysis tube (cut-off 12000-14000 Da) which was immersed in a container containing the receiving medium. The amount of Sorafenib in the receiving medium was detected by HPLC analysis.

Figure 2:
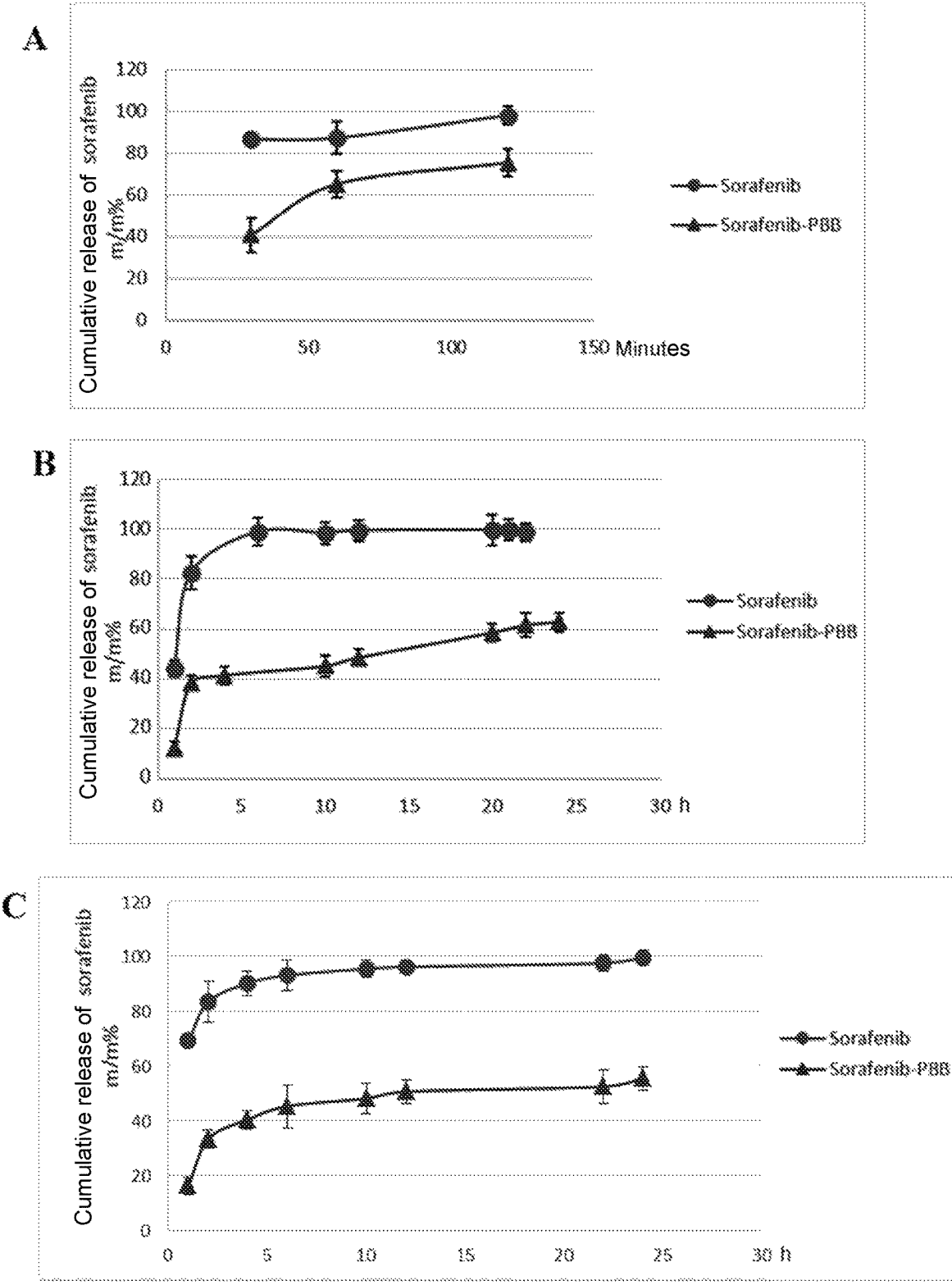
FIG. 2: Dissolution profile of free Sorafenib and Sorafenib release from the PBB nanoparticles in SGF for 2 hours (A); SIF for 24 hours (B) and PBS for 24 hours (C). The reported data refer to the mean values±SD (n=3).

The amount of released Sorafenib was expressed as a percentage ratio between the released drug weight and the total amount of Sorafenib loaded into the nanoparticles. FIG. 2 shows the release profiles of Sorafenib from Sorafenib PBB and the dissolution of the free drug in SGF (A), SIF (B) and PBS (C). It is observed, in panel A, that after 120 minutes incubation in SGF the cumulative release of Sorafenib from the nanoparticles was about 75%. The cumulative release of Sorafenib in 24 hours was about 63% in SIF (panel B) and about 55% in PBS (panel C). In the three release conditions, the dissolution of free Sorafenib is almost complete within two hours. Therefore, in all release media, Sorafenib PBB shows a prolonged release compared to the dissolution of free Sorafenib.

Example 5: In Vitro Biological Assays

Cell Lines:

The human hepatocellular carcinoma cell lines, HepG2 and Hep3B, were obtained from the American Type Culture Collection (ATCC). Cells were kept in 5% $CO_2$ and grown in Roswell Park Memorial Institute (RPMI) medium (SIGMA, Milan, Italy), supplemented with 10% (v/v) fetal bovine serum (FBS) (Gibco, Life Technologies, Monza MB, Italy), 2 mM L-glutamine, 100 U/ml of penicillin-streptomycin and 1 mM of sodium pyruvate (SIGMA, Milan, Italy). Cell lines were regularly checked for possible mycoplasma contamination.

Cell Viability Assays $5 \times 10^3$ cells/well were distributed in 96-well plates, dispensing 100 µl of cell suspension per well and incubated at 37° C. in 5% $CO_2$. The cells were incubated for further 72 hours with fresh medium containing free Sorafenib (Sorafenib tosylate solubilized in dimethyl sulfoxide, DMSO), Sorafenib PBB or empty PBB nanoparticles. The latter were resuspended in sterile conditions in sterile $H_2O$, sonicated for 20 min in a water sonicator, and diluted with a complete RPMI volume (2×). At the end of the treatment, cell viability assays were performed using the OneSolution aqueous CellTiter kit (Promega Corporation, Madison, Wis., USA). The percentage of cell viability was calculated with reference to the absorbance measured in the control cells. The experiments were performed in triplicate and the values expressed as mean±SD of three independent experiments. No bacterial growth was observed in any sample, confirming the complete sterility of the handling conditions and of the samples themselves.

Results measured after treatment with increasing concentrations (0.6-10 µM) of the indicated compounds are shown in FIG. 3. Cell viability is strongly decreased in a dose-dependent manner in the presence of free Sorafenib and, even more markedly, Sorafenib PBB.

Expression of Proteins Involved in Signaling and Apoptosis $3 \times 10^5$ cells/well were seeded in 6-well plates and kept for 24 hours at 37° C. in 5% $CO_2$. The cells were then treated for 24 hours with 2.5, 5 and 7.5 µM of free Sorafenib (solubilized in DMSO), empty PBB nanoparticles or Sorafenib PBB, solubilized as reported in cell viability assays. After treatment, cell lysates were obtained using the RIPA buffer (Cell Signaling Technologies Inc., Beverly, Mass., USA). The protein concentrations of the supernatants were determined with the Bio-Rad "Protein assay" kit (Bio-Rad Laboratories Srl, Milan, Italy). Western blotting analyzes were performed using as primary antibodies anti β-actin (SIGMA), anti ERK1/2, anti p-ERK1/2 (phospho-ERK1/2), anti PARP (poly(ADP)-ribose polymerase) and anti-Mcl-1 (myeloid cell leukemia 1) (Cell Signaling).

As shown in FIG. 4, free Sorafenib and Sorafenib PBB induce, at concentrations of 5 and 7.5 µM, the fragmentation of the PARP protein, indicative of the induction of apoptosis. Similarly, the decrease in the p-ERK1/2 signal is apparent after treatment with free Sorafenib and after treatment with Sorafenib PBB, especially at 7.5 µM concentration. A decrease in the expression levels of p-ERK1/2 is indicative of a decrease in cell proliferation. Inhibition of Mcl-1 expression levels, an anti-apoptotic protein, is apparent at the highest concentrations of free Sorafenib and Sorafenib PBB. Treatment with the carrier (PBB) alone does not show any effect on the expression levels of all the proteins analyzed.

Example 6: In Vivo Biological Assays

Mouse Model

Male nude mice (fox1 nu/nu) of 4 weeks of life were purchased at Envigo (Udine, Italy) and left to acclimatize for 1 week. Hep3B cells ($10 \times 10^6$ in 0.2 ml PBS), undergoing logarithmic growth, were inoculated in the right flank of the animals. When the tumors were palpable (about 300 mm³), the mice were randomly divided into four groups of five animals each, with the various tumor volumes equally distributed between the four groups. Each group was treated for 17 days as indicated below.

Group 1: daily treatment (6 days/week) by intraperitoneal (IP) injection with 10 mg/kg of Sorafenib tosylate resuspended in DMSO and further diluted in a 25% solution of ethanol (DMSO-EtOH).

Group 2: carrier only (DMSO-EtOH).

Group 3: daily treatment (6 days/week) with 10 mg/kg of Sorafenib PBB resuspended in RPMI.

Group 4: daily treatment (6 days/week) with 10 mg/kg of empty PBB nanoparticles resuspended in RPMI.

The lyophilized nanoparticle samples were resuspended and sonicated as reported in cell viability assays. Tumor volumes and body weight were recorded twice a week as previously described (Cusimano et al., *Cytotoxic activity of the novel small molecule AKT inhibitor SC66 in hepatocellular carcinoma cells*. Oncotarget 2015, 6, 1707-1722). The mice were sacrificed by cervical dislocation when the tumor mass exceeded 10% of the body weight of the animals, or when the tumor mass appeared ulcerated or other morbid conditions were found, in accordance with the institutional guidelines and in accordance with the national law (Legislative Decree No. 26 4-3-2014) and international laws and policies (ECC Council Directive 86/609, OJ L358.1, Dec. 12, 1987). This study was authorized by the Ministry of Health with authorization number 1187/2015-PR. At the end of the trial, tumors, liver, kidneys, lungs and spleen were collected from each animal. Half of each tumor, or organ, was frozen in liquid nitrogen and stored at −80° C. for biodistribution analyzes, while the other half was fixated in formalin and used for immunohistochemistry analysis.

Immunohistochemistry Analysis

To quantify the Ki-67 cell proliferation marker expression, the ImmunoRatio® software (http://jvsmicroscope.u-ta.fi/immunoratio/) was used which, using a color deconvolution algorithm, calculates the percentage of positively marked area (area stained with diaminobenzidine) towards the total nuclear area. The hematoxylin stains were also acquired to analyze the neo-vascularization of the tumor, using the Leica DMR microscope equipped with a Leica DFC 320 digital camera.

Figure 5:
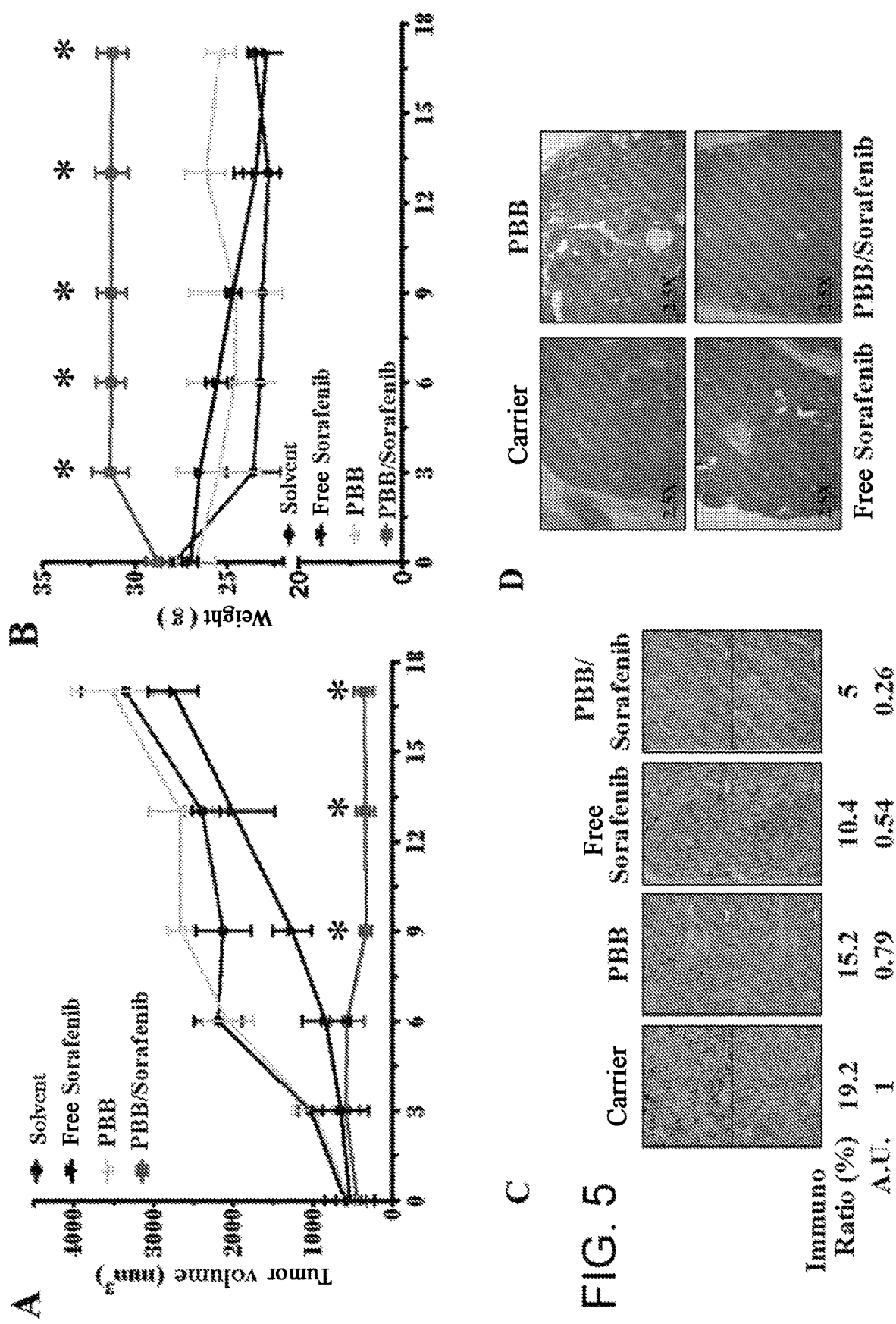
FIG. 5: In vivo therapeutic efficacy of Sorafenib PBB in human xenografting models of Hep3B hepatocellular carcinoma and comparison with free Sorafenib. (A) Growth of the tumor *p<0.05. (B) Analysis of the alteration of body weight. (C) Proliferation index, by analysis of Ki67 protein expression levels, of tumor tissues from control mice and treated mice. The data are expressed as a percentage of positively colored nuclei/total cells. Bar=50 µm. (D) Hematoxylin staining of blood vessels in tumor tissues of control mice and treated mice.

As shown in FIG. 5A, treatment with 10 mg/kg of free form Sorafenib reduced tumor growth compared to the carrier alone, although this difference was not significant. Treatment with Sorafenib PBB significantly inhibited tumor growth compared to treatment with the free drug ($p<0.05$). During treatment, changes in the body weight of the animal were also monitored. As shown in FIG. 5B, mice treated with 10 mg/kg of Sorafenib did not show a significant loss of body weight, compared to mice treated with the carrier alone, suggesting a satisfactory level of cytotoxicity of the drug at the concentration used in this study. Mice treated with Sorafenib PBB showed a significant increase in their body weight ($p<0.001$).

Mobility was also assessed in treated animals, observing better physical mobility in the group of animals treated with Sorafenib PBB.

To evaluate the anti-proliferative activity, the expression levels of the Ki67 nuclear marker were analyzed. The number of Ki67-positive cells decreases in tumor tissues from animals treated with Sorafenib PBB compared to that in tumor tissues of animals treated with the free drug, with empty PBBs or with carrier alone (FIG. 5C). Furthermore, the tumor vascularization was evaluated in tumor tissues after staining of blood vessels with hematoxylin (FIG. 5D).

The number and size of blood vessels decreases dramatically in tumor tissues from animals treated with Sorafenib PBB compared to those seen in the tissues of animals treated with free drug, with empty PBBs or with the carrier alone.

Biodistribution Studies

Sorafenib was extracted from the tissues of the treated animals following the procedure described in Craparo E F et al. *Galactosylated polymeric carriers for liver targeting of Sorafenib*. Int J Pharm 2014, 466, 172-180. Briefly, each tissue sample was mixed with Tris buffer (2 ml, 1 M, pH 8) in a 15 ml glass tube and homogenized using an Ultraturrax T 25 (Janke & Kunkel Ika—Labortechnik) at 20500 rpm for 15 min. Then, methanol (1 ml) was added to precipitate the proteins. The samples were extracted three times with ethyl ether (2 ml), and each extraction was followed by centrifugation at 4000 rpm for 5 min at room temperature. After each addition of solvent, the centrifuge tubes were stirred for 15 min at room temperature and centrifuged for 5 min at 4000 rpm. The organic layers were transferred to a glass tube and evaporated to dryness.

Each dry residue was treated with methanol (0.6 ml) and, after stirring, a volume of 50 µl was injected into the HPLC system. The data shown in FIG. 6 surprisingly show an accumulation of Sorafenib in the analyzed organs such as liver, spleen, lungs and kidneys and said accumulation decreases when the animals are treated with Sorafenib PBB (gray column) compared to when treatment is performed with free Sorafenib (white column). In particular, the amount of Sorafenib detected when mice were treated with the free drug was significantly higher in the kidneys ($p<0.05$), spleen ($p<0.05$) and lungs ($p<0.01$) than the accumulation occurring after the administration of Sorafenib PBB.

Advantageously, Sorafenib PBB preferentially accumulates in the tumor tissue. In fact, the amount of Sorafenib detected in the tumor after the administration of Sorafenib PBB was found to be abundantly higher than that detected after the injection of free Sorafenib, and this difference is highly significant ($p<0.01$).

What is claimed is:

1. Nanoparticles loaded with Sorafenib (Sorafenib PBB) or Sorafenib derivatives or pharmaceutically acceptable salts thereof (Sorafenib PBB derivatives), wherein said nanoparticles are polymeric PBB nanoparticles, (PHEA-BIB-pButMA, α,β-poly(N-2-hydroxyethyl)-co-{N-2-ethylene-[2-(poly(butylmethacrylate)-isobutyrate]}-D,L-aspartamide).

2. The nanoparticles according to claim 1, having a diameter of less than 500 nm.

3. The nanoparticles according claim 1, having a Drug loading % (DL %) between 0.5 and 30%.

4. The nanoparticles according to claim 1, wherein said Sorafenib derivatives are selected from the group consisting of:

Regorafenib, of formula (1)

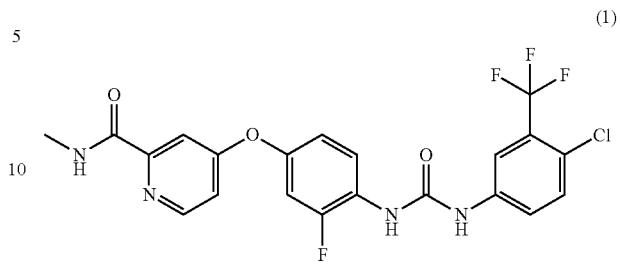

SC-60 of formula (2)

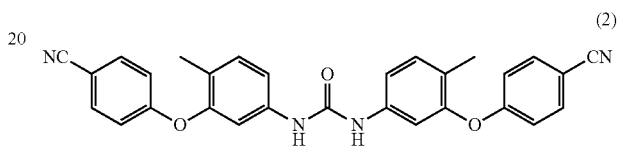

HLC-80, of formula (3)

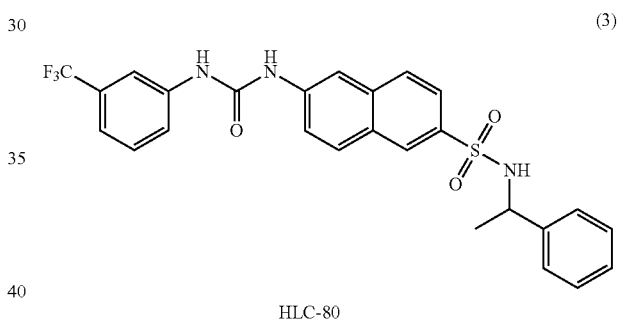

HLC-80 compounds of formula (4), where R1, R2, and R3 are as indicated in the following table:

(4)

| Cpd | $R_1$ | $R_2$ | $R_3$ |
|---|---|---|---|
| SC-1 | ![Cl, CF3 substituted phenyl urea] | | |

-continued

| Cpd | R₁ | R₂ | R₃ |
|---|---|---|---|
| 1 | ~NH-C(=O)-NH-CH₂-(3,4-dimethoxyphenyl) | H | H |
| 2 | ~CH₂-NH-C(=O)-NH-(4-chloro-3-trifluoromethylphenyl) | H | H |
| 3 | ~CH₂-NH-C(=O)-NH-CH₂-(3,4-dimethoxyphenyl) | H | H |
| 4 | ~CH₂-NH-C(=O)-NH-CH₂-(3-trifluoromethoxyphenyl) | H | H |
| 5 | ~NH-C(=O)-NH-CH(CH₃)-(1-naphthyl) | H | H |
| 6 | H | ~NH-C(=O)-NH-(4-chloro-3-trifluoromethylphenyl) | H |
| 7 | H | ~NH-S(=O)₂-(3-trifluoromethylphenyl) | H |
| 8 | H | ~NH-CH₂-(3-trifluoromethoxyphenyl) | H |

-continued

| Cpd | R₁ | R₂ | R₃ |
|---|---|---|---|
| 9 | H | 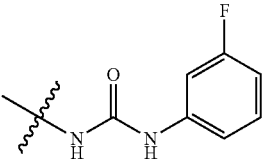 [SMILES: *NC(=O)Nc1cccc(F)c1] 3-fluorophenyl urea linker | H |
| 10 | H | 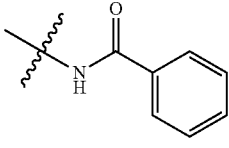 [SMILES: *NC(=O)c1ccccc1] benzamide linker | H |
| 11 | H | 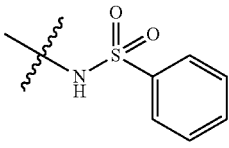 [SMILES: *NS(=O)(=O)c1ccccc1] phenylsulfonamide linker | H |
| 12 | H | 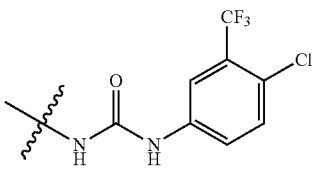 [SMILES: *NC(=O)Nc1ccc(Cl)c(C(F)(F)F)c1] 4-chloro-3-(trifluoromethyl)phenyl urea linker | Me | compounds of formula (5), where R1 and R2 are as indicated in the following table

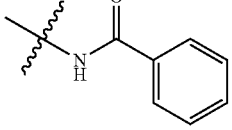

(5)

| Cpd | R₁ | R₂ |
|---|---|---|
| 13 | H | 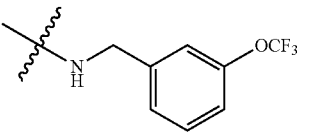 [SMILES: *NCc1cccc(OC(F)(F)F)c1] 3-fluorophenyl urea linker |
| 14 | H | 3-(trifluoromethyl)phenylsulfonamide linker |
| 15 | H | benzamide linker |
| 16 | H | 3-(trifluoromethoxy)benzylamine linker |
| 17 | H | 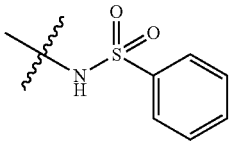 phenylsulfonamide linker | compounds of formula (6) where R1, R2 and R3 are as indicated in the following table (6)

[Structure of formula (6): phenyl ring with R1 (para) and R2 (meta) substituents, connected via ether oxygen to another phenyl ring bearing R3]

| Cpd | R₁ | R₂ | R₃ |
|---|---|---|---|
| 18 | NO₂ | NH₂ | -NH-CH₂-(3-OCF₃-phenyl) |
| 19 | NO₂ | NH₂ | -NH-SO₂-(3-CF₃-phenyl) |
| 20 | NO₂ | NH₂ | -NH-C(O)-NH-(4-Cl-3-CF₃-phenyl) |
| 21 | NH₂ | NH₂ | -NH-CH₂-(3-OCF₃-phenyl) |
| 22 | NH₂ | NH₂ | -NH-SO₂-(3-CF₃-phenyl) |
| 23 | -NH-C(O)-NH- (urea linker) | | -NH-CH₂-(3-OCF₃-phenyl) |
| 24 | -NH-C(O)-NH- (urea linker) | | -NH-SO₂-(3-CF₃-phenyl) | compounds of formula (7) where R1 and R2 are as indicated in the following table (7)

[Structure of formula (7): R2-NH-C(O)-NH-phenyl-O-pyridine-C(O)-NH-NH-C(O)-CH=CH-R1]

| Compound | R₂ | R₁ |
|---|---|---|
| Sorafenib | — | — |
| 8a | 4-Chloro-3-trifluoromethylphenyl | Phenyl |
| 8b | 4-Chloro-3-trifluoromethylphenyl | 2-Furyl |
| 8c | 4-Chloro-3-trifluoromethylphenyl | 3-Furyl |
| 8d | 4-Chloro-3-trifluoromethylphenyl | 2-Thienyl |
| 8e | 4-Chloro-3-trifluoromethylphenyl | Pyridine-3-yl |
| 8f | 4-Chloro-3-trifluoromethylphenyl | 4-Hydroxyphenyl |
| 8 g | 4-Chloro-3-trifluoromethylphenyl | 4-Methoxyphenyl |
| 8 h | 4-Chloro-3-trifluoromethylphenyl | 4-Chlorophenyl |
| 8i | 4-Chloro-3-trifluoromethylphenyl | 4-Trifluoromethylphenyl |
| 8j | 4-Chloro-3-trifluoromethylphenyl | 4-Carbomethoxyphenyl |
| 8k | 4-Chloro-3-trifluoromethylphenyl | 3-Hydroxyphenyl |
| 8l | 4-Chloro-3-trifluoromethylphenyl | 3-Chlorophenyl |
| 8m | 4-Chloro-3-trifluoromethylphenyl | 3-Trifluoromethylphenyl |
| 8n | 4-Chloro-3-trifluoromethylphenyl | 4-Hydroxyl-3-methoxylphenyl |
| 8o | 4-Chloro-3-trifluoromethylphenyl | 3,4-Bimethoxylphenyl |
| 8p | 4-Chloro-3-trifluoromethylphenyl | 4-Acetoxy-3-methoxylphenyl |
| 8q | 4-Chloro-3-trifluoromethylphenyl | 3,4-Biflourophenyl |
| 8r | 4-Chloro-3-trifluoromethylphenyl | 2,4-Bichlorophenyl |
| 8 s | 4-Chloro-3-trifluoromethylphenyl | 2,3,4,5,6-Pentafluorophenyl |
| 11a | 4-Chlorophenyl | 4-Chlorophenyl |
| 11b | 4-Flurophenyl | 4-Chlorophenyl |
| 11c | 4-Trifluoromethylphenyl | 4-Chlorophenyl |
| 11d | 4-Ethoxylphenyl | 4-Chlorophenyl |
| 11e | 3-Methylphenyl | 4-Chlorophenyl |
| 11f | 3-Bromophenyl | 4-Chlorophenyl |
| 11g | 3-Chloro-4-methylphenyl | 4-Chlorophenyl |
| 11h | 2,4-Biflourophenyl | 4-Chlorophenyl | compounds 12 and 13 of formula (8) and compounds 14a-k and 15a-k of formula (9) and (10), where R is as indicated in the following table
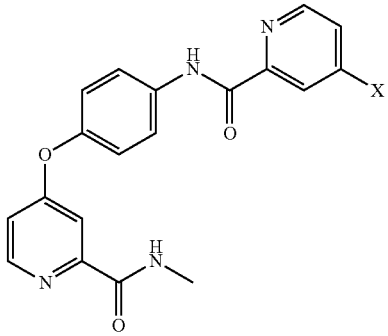
(8)
12, X = Cl
13, X = Br
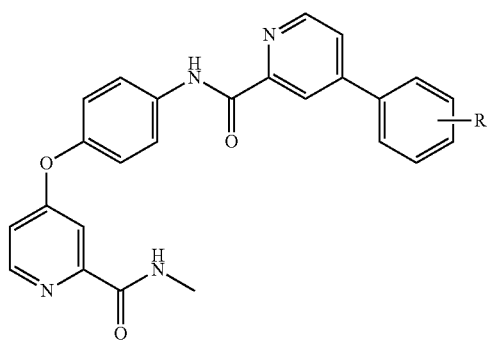
(9)
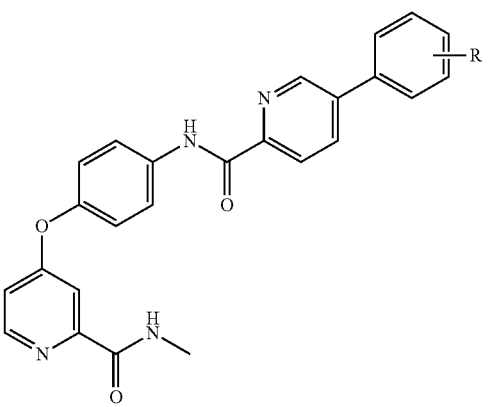
(10)
| Comp. no. | R |
|---|---|
| 12 | — |
| 13 | — |
| 14a | H |
| 14b | 4-F |
| 14c | 2,4-di F |
| 14d | 4-Cl |
| 14e | 4-OCH$_3$ |
| 14f | 4-CH$_3$ |
| 14g | 3-CH$_3$ |
| 14h | 3-F |
| 14i | 4-CF$_3$ |
| 14j | 4-CH$_2$CH$_3$ |
| 14k | 2,4-di CH$_3$ |
| 15a | H |
-continued
| Comp. no. | R |
|---|---|
| 15b | 4-F |
| 15c | 2,4-di F |
| 15d | 4-Cl |
| 15e | 4-OCH$_3$ |
| 15f | 4-CH$_3$ |
| 15g | 3-CH$_3$ |
| 15h | 3-F |
| 15i | 4-CF$_3$ |
| 15j | 4-CH$_2$CH$_3$ |
| 15k | 2,4-di CH$_3$ |
compounds 2a-e, 3a-e, 4a-e of formula (11), (12) and (13), where R is as indicated in the following table
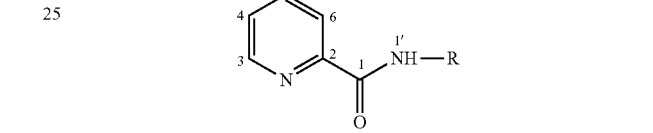
(11)
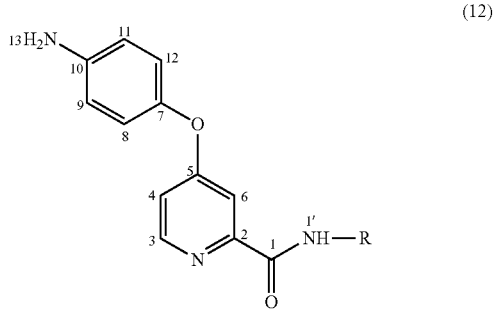
(12)
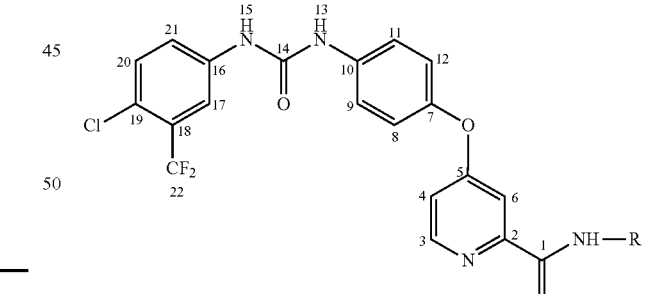
(13)
| Compd. | R |
|---|---|
| 2a | <img> |

-continued

| Compd. | R |
|---|---|
| 2b | 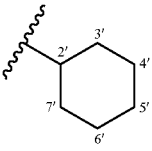 |
| 2c | 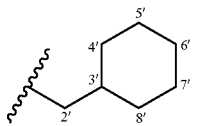 |
| 2d | 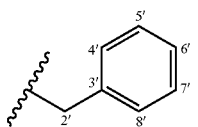 |
| 2e | 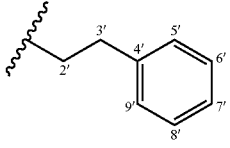 |
| 3a | 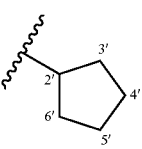 |
| 3b | 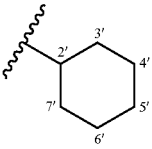 |
| 3c | 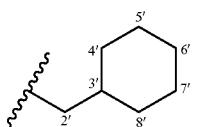 |
| 3d | 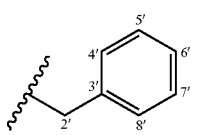 |
| 3e | 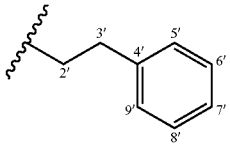 |

-continued

| Compd. | R |
|---|---|
| 4a | 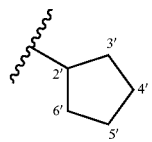 [SMILES: *C1CCCC1] |
| 4b | 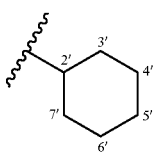 [SMILES: *C1CCCCC1] |
| 4c | 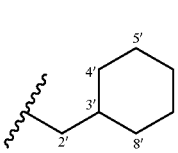 |
| 4d | 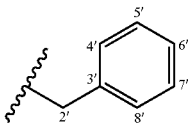 |
| 4e | 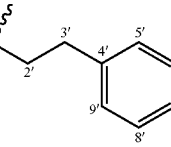 | compounds of formula (14) where R is as indicated in the following table

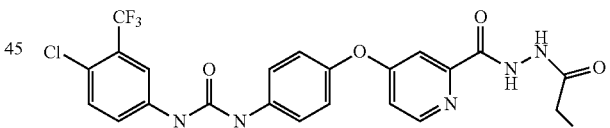

(14)

| Compd. | Substituent (R) |
|---|---|
| 5a | $C_6H_4$ |
| 5b | $4\text{-}ClC_6H_4$ |
| 5c | $3\text{-}ClC_6H_4$ |
| 5d | $2\text{-}ClC_6H_4$ |
| 5e | $3\text{-}CF_3C_6H_4$ |
| 5f | $4\text{-}CF_3C_6H_4$ |
| 5g | $3\text{-}FC_6H_4$ |
| 5h | $4\text{-}FC_6H_4$ |
| 5i | $3\text{-}F\text{-}5\text{-}FC_6H_3$ |
| 5j | $3\text{-}F\text{-}4\text{-}BrC_6H_3$ |
| 5k | $2\text{-}F\text{-}3\text{-}FC_6H_3$ |
| 5l | $3\text{-}Cl\text{-}4\text{-}OHC_6H_3$ |
| 5m | $2\text{-}OMeC_6H_4$ |
| 5n | $3\text{-}OMe\text{-}4\text{-}OMeC_6H_3$ |
| 5o | $4\text{-}OEtC_6H_4$ |
| 5p | 2-Naphthyl |

-continued

| Compd. | Substituent (R) |
|---|---|
| 5q | 4-C$_6$H$_5$—C$_6$H$_4$ |
| 5r | 4-MeC$_6$H$_4$. |

5. A method for preparing Sorafenib PBB or Sorafenib PBB derivatives, wherein the method comprises:
- a) providing a copolymer α,β-poly(N-2-hydroxyethyl)-co-{N-2-ethylene-[2-(poly(butylmethacrylate)-isobutyrate]}-D,L-aspartamide (PBB) and Sorafenib or salts and derivatives thereof;
- b) dissolving in a solvent;
- c) dialyzing against aqueous phase using a dialysis membrane with a molecular weight (MW) cut-off greater than a MW of the copolymer to obtain a colloidal dispersion; and
- d) Filtering the colloidal dispersion obtained in c) to obtain Sorafenib PBB or Sorafenib PBB derivatives.

6. The method according to claim 5, wherein said Sorafenib is Sorafenib tosylate.

7. The method according to claim 5, wherein said Sorafenib derivatives are selected from the group comprising:

Regorafenib, of formula (1)

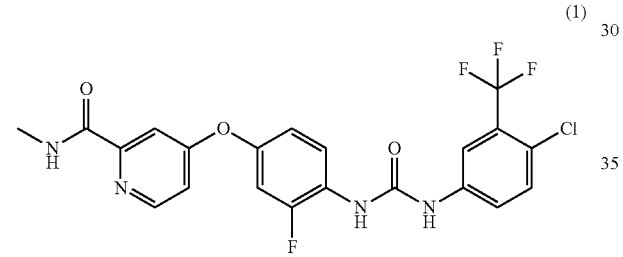

SC-60 of formula (2)

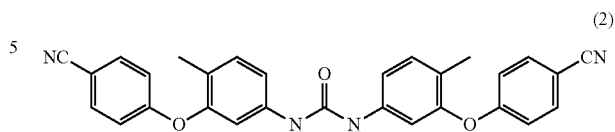

HLC-80, of formula (3)

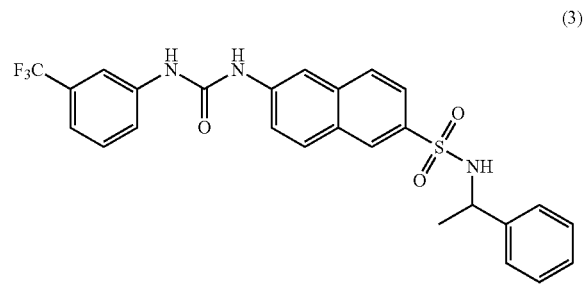

HLC-080 compounds of formula (4), where R1, R2 and R3 are as indicated in the following table:

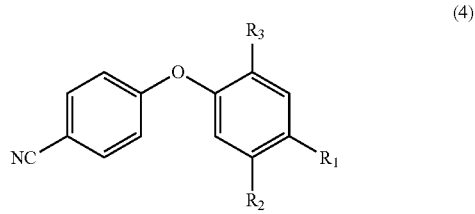

| Cpd | R$_1$ | R$_2$ | R$_3$ |
|---|---|---|---|
| SC-1 | 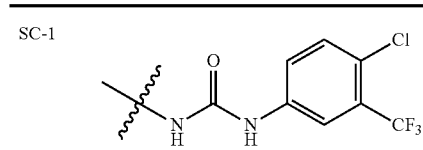 | | |
| 1 | 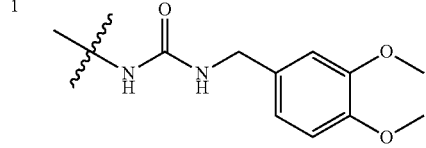 | H | H |
| 2 | 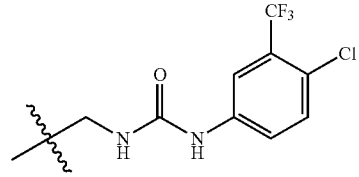 [SMILES: *CNC(=O)Nc1ccc(Cl)c(C(F)(F)F)c1] | H | H |

-continued
| Cpd | R₁ | R₂ | R₃ |
|---|---|---|---|
| 3 | 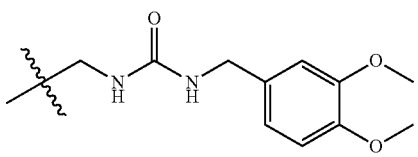 [SMILES: *CNC(=O)NCc1ccc(OC)c(OC)c1] | H | H |
| 4 | 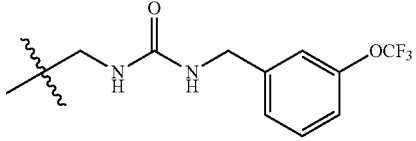 [SMILES: *CNC(=O)NCc1cccc(OC(F)(F)F)c1] | H | H |
| 5 | 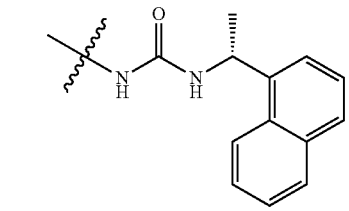 [SMILES: *NC(=O)N[C@H](C)c1cccc2ccccc12] | H | H |
| 6 | H | 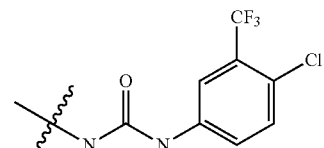 | H |
| 7 | H | 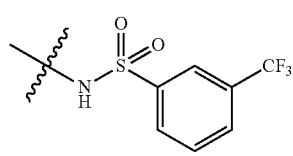 [SMILES: *NS(=O)(=O)c1cccc(C(F)(F)F)c1] | H |
| 8 | H | 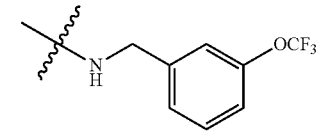 [SMILES: *NCc1cccc(OC(F)(F)F)c1] | H |
| 9 | H | 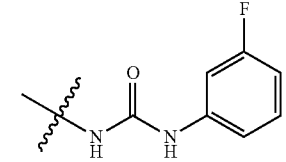 [SMILES: *NC(=O)Nc1cccc(F)c1] | H |
| 10 | H | 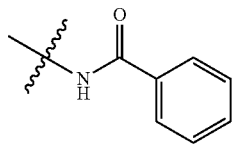 [SMILES: *NC(=O)c1ccccc1] | H |
| 11 | H | 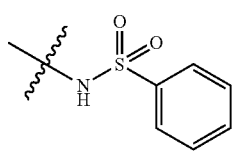 [SMILES: *NS(=O)(=O)c1ccccc1] | H |

-continued

| Cpd | R₁ | R₂ | R₃ |
|---|---|---|---|
| 12 | H | (urea linked to 4-chloro-3-trifluoromethylphenyl) | Me | compounds of formula (5), where R1 and R2 are as indicated in the following table (5)

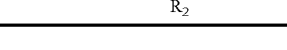

| Cpd | R₁ | R₂ |
|---|---|---|
| 13 | H | urea-NH-C(=O)-NH-(3-fluorophenyl) |
| 14 | H | sulfonamide -NH-SO₂-(3-CF₃-phenyl) |
| 15 | H | amide -NH-C(=O)-phenyl |
| 16 | H | -NH-CH₂-(3-OCF₃-phenyl) |
| 17 | H | -NH-SO₂-phenyl | compounds of formula (6) where R1, R2 and R3 are as indicated in the following table (6)

| Cpd | R₁ | R₂ | R₃ |
|---|---|---|---|
| 18 | NO₂ | NH₂ | -NH-CH₂-(3-OCF₃-phenyl) |
| 19 | NO₂ | NH₂ | -NH-SO₂-(3-CF₃-phenyl) |
| 20 | NO₂ | NH₂ | -NH-C(=O)-NH-(4-Cl-3-CF₃-phenyl) |
| 21 | NH₂ | NH₂ | -NH-CH₂-(3-OCF₃-phenyl) |
| 22 | NH₂ | NH₂ | -NH-SO₂-(3-CF₃-phenyl) |

-continued

| Cpd | R₁ | R₂ | R₃ |
|---|---|---|---|
| 23 | 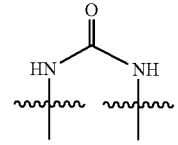 [SMILES: *NC(=O)N*] | | 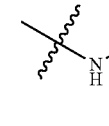 |
| 24 | 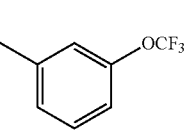 | | 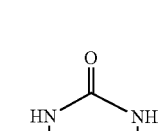 | compounds of formula (7) where R1 and R2 are as indicated in the following table

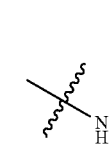
(7)

| Compound | R₂ | R₁ |
|---|---|---|
| Sorafenib | — | — |
| 8a | 4-Chloro-3-trifluoromethylphenyl | Phenyl |
| 8b | 4-Chloro-3-trifluoromethylphenyl | 2-Furyl |
| 8c | 4-Chloro-3-trifluoromethylphenyl | 3-Furyl |
| 8d | 4-Chloro-3-trifluoromethylphenyl | 2-Thienyl |
| 8e | 4-Chloro-3-trifluoromethylphenyl | Pyridine-3-yl |
| 8f | 4-Chloro-3-trifluoromethylphenyl | 4-Hydroxyphenyl |
| 8 g | 4-Chloro-3-trifluoromethylphenyl | 4-Methoxylphenyl |
| 8 h | 4-Chloro-3-trifluoromethylphenyl | 4-Chlorophenyl |
| 8i | 4-Chloro-3-trifluoromethylphenyl | 4-Trifluoromethylphenyl |
| 8j | 4-Chloro-3-trifluoromethylphenyl | 4-Carbomethoxyphenyl |
| 8k | 4-Chloro-3-trifluoromethylphenyl | 3-Hydroxyphenyl |
| 8l | 4-Chloro-3-trifluoromethylphenyl | 3-Chlorophenyl |
| 8m | 4-Chloro-3-trifluoromethylphenyl | 3-Trifluoromethylphenyl |
| 8n | 4-Chloro-3-trifluoromethylphenyl | 4-Hydroxyl-3-methoxylphenyl |
| 8o | 4-Chloro-3-trifluoromethylphenyl | 3,4-Bimethoxylphenyl |
| 8p | 4-Chloro-3-trifluoromethylphenyl | 4-Acetoxy-3-methoxylphenyl |
| 8q | 4-Chloro-3-trifluoromethylphenyl | 3,4-Bifluorophenyl |
| 8r | 4-Chloro-3-trifluoromethylphenyl | 2,4-Bichlorophenyl |
| 8 s | 4-Chloro-3-trifluoromethylphenyl | 2,3,4,5,6-Pentafluorophenyl |
| 11a | 4-Chlorophenyl | 4-Chlorophenyl |
| 11b | 4-Flurophenyl | 4-Chlorophenyl |
| 11c | 4-Trifluoromethylphenyl | 4-Chlorophenyl |
| 11d | 4-Ethoxylphenyl | 4-Chlorophenyl |
| 11e | 3-Methylphenyl | 4-Chlorophenyl |
| 11f | 3-Bromophenyl | 4-Chlorophenyl |
| 11g | 3-Chloro-4-methylphenyl | 4-Chlorophenyl |
| 11h | 2,4-Biflourophenyl | 4-Chlorophenyl | compounds 12 and 13 of formula (8) and compounds 14a-k and 15a-k of formula (9) and (10), where R is as indicated in the following table

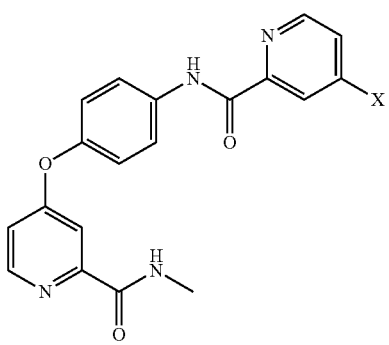
(8)

12, X = Cl
13, X = Br

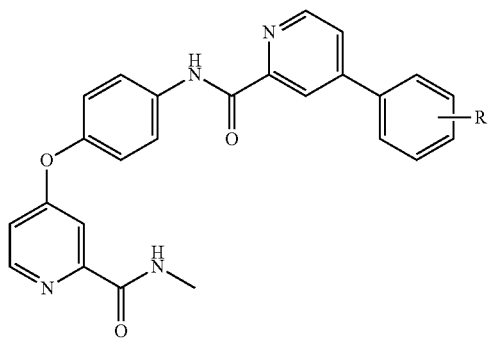
(9)

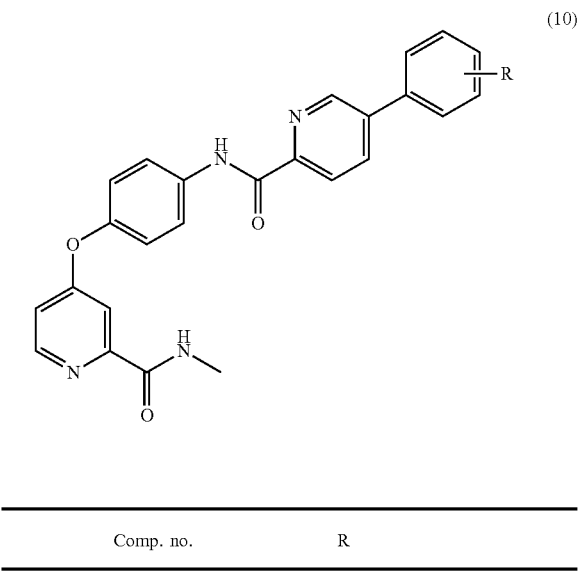
| Comp. no. | R |
|---|---|
| 12 | — |
| 13 | — |
| 14a | H |
| 14b | 4-F |
| 14c | 2,4-di F |
| 14d | 4-Cl |
| 14e | 4-OCH$_3$ |
| 14f | 4-CH$_3$ |
| 14g | 3-CH$_3$ |
| 14h | 3-F |
| 14i | 4-CF$_3$ |
| 14j | 4-CH$_2$CH$_3$ |
| 14k | 2,4-di CH$_3$ |
| 15a | H |
| 15b | 4-F |
| 15c | 2,4-di F |
| 15d | 4-Cl |
| 15e | 4-OCH$_3$ |
| 15f | 4-CH$_3$ |
| 15g | 3-CH$_3$ |
| 15h | 3-F |
| 15i | 4-CF$_3$ |
| 15j | 4-CH$_2$CH$_3$ |
| 15k | 2,4-di CH$_3$ |
compounds 2a-e, 3a-e, 4a-e of formula (11), (12) and (13), where R is as indicated in the following table
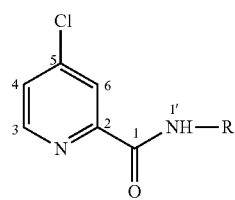
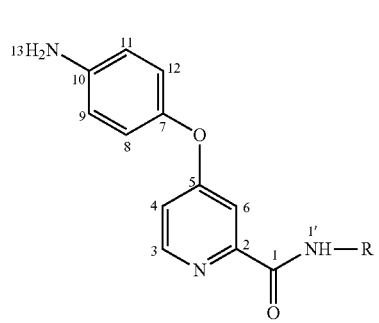
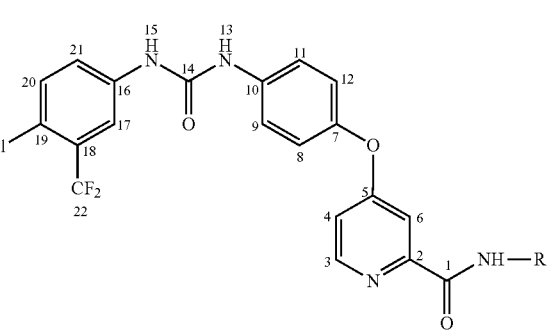
| Compd. | R |
|---|---|
| 2a | 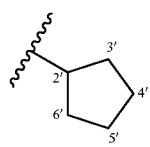 |
| 2b | 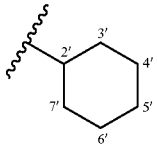 [SMILES: *C1CCCCC1] |
| 2c | 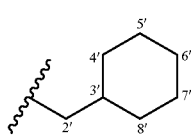 |
| 2d | 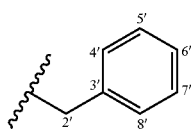 |
| 2e | 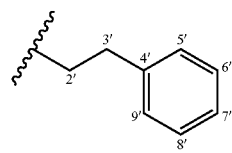 [SMILES: *CCc1ccccc1] |

-continued

| Compd. | R |
|---|---|
| 3a | 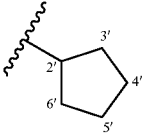 |
| 3b | 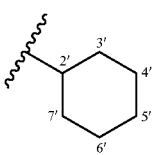 [SMILES: *C1CCCCC1] |
| 3c | 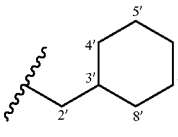 |
| 3d | 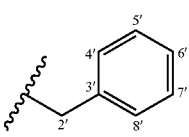 |
| 3e | 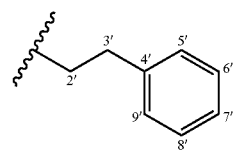 |
| 4a | 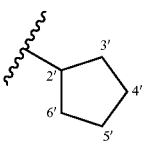 |
| 4b | 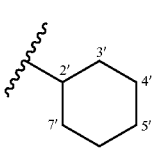 |
| 4c | 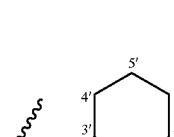 |
| 4d | 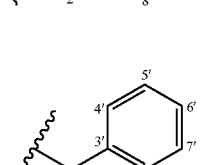 |

-continued

| Compd. | R |
|---|---|
| 4e | 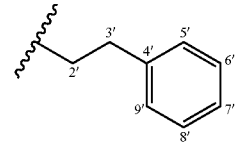 [SMILES: *CCc1ccccc1] | compounds of formula (14) where R is as indicated in the following table (14)

[Structure of formula (14)]

| Compd. | Substituent (R) |
|---|---|
| 5a | $C_6H_4$ |
| 5b | $4\text{-}ClC_6H_4$ |
| 5c | $3\text{-}ClC_6H_4$ |
| 5d | $2\text{-}ClC_6H_4$ |
| 5e | $3\text{-}CF_3C_6H_4$ |
| 5f | $4\text{-}CF_3C_6H_4$ |
| 5g | $3\text{-}FC_6H_4$ |
| 5h | $4\text{-}FC_6H_4$ |
| 5i | $3\text{-}F\text{-}5\text{-}FC_6H_3$ |
| 5j | $3\text{-}F\text{-}4\text{-}BrC_6H_3$ |
| 5k | $2\text{-}F\text{-}3\text{-}FC_6H_3$ |
| 5l | $3\text{-}Cl\text{-}4\text{-}OHC_6H_3$ |
| 5m | $2\text{-}OMeC_6H_4$ |
| 5n | $3\text{-}OMe\text{-}4\text{-}OMeC_6H_3$ |
| 5o | $4\text{-}OEtC_6H_4$ |
| 5p | 2-Naphthyl |
| 5q | $4\text{-}C_6H_5\text{—}C_6H_4$ |
| 5r | $4\text{-}MeC_6H_4$. |

8. The method according to claim 5, wherein said solvent is DMF (dimethylformamide) or DMSO (dimethyl sulfoxide) or THF (tetrahydrofuran), or mixtures thereof.

9. The method according to claim 5, wherein after said step c), a cryoprotectant is added to said colloidal dispersion.

10. The method according to claim 5, wherein the weight ratio of said PBB copolymer to said Sorafenib is between 10:1 and 1:1.

11. A controlled release formulation of Sorafenib or derivatives thereof comprising Sorafenib PBB or Sorafenib PBB derivatives or pharmaceutically acceptable salts.

12. The formulation according to claim 11, further comprising an effective amount of one or more further therapeutic agents.

13. A method of treating tumor diseases of the kidney, liver, thyroid, colon, breast, pancreas, lungs, and/or of recurrent glioblastoma, the method comprising administering the formulation according to claim 11 to a patient or a subject affected by said tumor diseases.

14. The method according to claim 13, wherein the tumor disease is hepatocellular carcinoma.

15. The nanoparticles according to claim 2, having a diameter of less than 300 nm.

16. The nanoparticles according to claim 3, having a DL % between about 3 and 20%.

17. The method according to claim 5, wherein the 1\4W of the copolymer is greater than 80,000 Da.

18. The method according to claim 9, wherein the cyroprotectant is selected from the group consisting of PVP (polyvinylpyrrolidone), PVA (polyvinyl alcohol), trehalose, mid/or lactose, and mixtures thereof.

19. The method according to claim 10, wherein the weight ratio of said PBB copolymer to said Sorafenib is between 6:1 and 1.5:1.

20. The method according to claim 19, wherein the weight ratio of said PBB copolymer to said Sorafenib is 2:1.

* * * * *